(12) United States Patent
Radu et al.

(10) Patent No.: US 7,838,627 B2
(45) Date of Patent: Nov. 23, 2010

(54) COMPOSITIONS COMPRISING NOVEL COMPOUNDS AND POLYMERS, AND ELECTRONIC DEVICES MADE WITH SUCH COMPOSITIONS

(75) Inventors: Nora Sabina Radu, Landenberg, PA (US); Gary A. Johansson, Hockessin, DE (US); Norman Herron, Newark, DE (US); Troy C. Gehret, Wilmington, DE (US)

(73) Assignee: E. I. du Pont de Nemours and Company, Wilmington, DE (US)

( * ) Notice: Subject to any disclaimer, the term of this patent is extended or adjusted under 35 U.S.C. 154(b) by 728 days.

(21) Appl. No.: 11/643,293

(22) Filed: Dec. 21, 2006

(65) Prior Publication Data
US 2007/0232782 A1 Oct. 4, 2007

Related U.S. Application Data

(60) Provisional application No. 60/754,976, filed on Dec. 29, 2005.

(51) Int. Cl.
*C08G 73/00* (2006.01)
(52) U.S. Cl. .................................. 528/422; 564/305
(58) Field of Classification Search ................. 528/422; 564/305
See application file for complete search history.

(56) References Cited

U.S. PATENT DOCUMENTS

| | | | |
|---|---|---|---|
| 5,962,631 A | 10/1999 | Woo et al. | |
| 6,303,238 B1 | 10/2001 | Thompson et al. | |
| 6,800,722 B2 | 10/2004 | Pei | ............... 528/423 |
| 2001/0019782 A1 | 9/2001 | Igarashi et al. | |
| 2004/0029133 A1 | 2/2004 | Herrnstadt | |
| 2004/0254297 A1 | 12/2004 | Hsu et al. | |
| 2005/0260448 A1 | 11/2005 | Lin | ............... 428/690 |
| 2009/0206327 A1* | 8/2009 | Radu et al. | ............... 257/40 |

FOREIGN PATENT DOCUMENTS

| | | | |
|---|---|---|---|
| EP | 650955 A1 * | 5/1995 |
| EP | 1191612 A2 | 3/2002 |
| EP | 1191614 A2 | 3/2002 |
| WO | 00/53565 A1 | 9/2000 |
| WO | 00/70655 A2 | 11/2000 |
| WO | 0141512 A1 | 6/2001 |
| WO | 02/02714 A2 | 1/2002 |
| WO | 02/15645 A1 | 2/2002 |

OTHER PUBLICATIONS

I. H. Campbell et al., Excitation Transfer Processes in a Phosphor-Doped Poly(P-Phenylene Vinylene) Light-Emitting Diode, Physical Review B, vol. 65:085210-1-085210-8, 2002.
D. F. O'Brien et al., Electrophorescence From a Doped Polymer Light Emitting Diode, Synthetic Metals, vol. 116:379-383, 2001.
G. Gustafsson et al., Flexible Light-Emitting Diodes Made From Soluble Conducting Polymers, Nature, vol. 357:477-479, 1992.
I. Colon et al., High Molecular Weight Aromatic Polymers by Nickel Coupling of Aryl Polychlorides, J. of Polymer Science Part A: Polymer Chemistry, vol. 28:367-383, 1990.
Takakazu Yamamoto, Electrically Conducting and Thermally Stable n-Conjugated Poly (Arylene)s Prepared by Organometallic Processes, Prog. Polym. Sci., vol. 17:1153-1205, 1992.
CRC Handbook of Chemistry and Physics, 81st Edition, 2000 (Book Not Included).

* cited by examiner

*Primary Examiner*—Randy Gulakowski
*Assistant Examiner*—Shane Fang
(74) *Attorney, Agent, or Firm*—John H. Lamming

(57) ABSTRACT

The present invention relates to novel compounds and polymers, compositions comprising novel compounds or polymers, and electronic devices comprising at least one layer containing the compound or polymer.

15 Claims, 5 Drawing Sheets

COMPOSITIONS COMPRISING NOVEL COMPOUNDS AND POLYMERS, AND ELECTRONIC DEVICES MADE WITH SUCH COMPOSITIONS

CROSS REFERENCE TO RELATED APPLICATION

This application claims priority under 35 U.S.C. §119(e) from U.S. Provisional Application No. 60/754,976, filed on Dec. 29, 2005, which is incorporated by reference as if fully set forth herein.

BACKGROUND OF THE INVENTION

1. Field of the Invention

The present invention relates to novel compounds useful as hole transport materials in making electronic devices. The invention further relates to electronic devices having at least one active layer comprising such a hole transport compound.

2. Background

In organic photoactive electronic devices, such as organic light emitting diodes ("OLED"), that make up OLED displays, the organic active layer is sandwiched between two electrical contact layers in an OLED display. In an OLED the organic photoactive layer emits light through the light-transmitting electrical contact layer upon application of a voltage across the electrical contact layers.

It is well known to use organic electroluminescent compounds as the active component in light-emitting diodes. Simple organic molecules, conjugated polymers, and organometallic complexes have been used.

Devices that use photoactive materials frequently include one or more charge transport layers, which are positioned between a photoactive (e.g., light-emitting) layer and a contact layer (hole-injecting contact layer). A device can contain two or more contact layers. A hole transport layer can be positioned between the photoactive layer and the hole-injecting contact layer. The hole-injecting contact layer may also be called the anode. An electron transport layer can be positioned between the photoactive layer and the electron-injecting contact layer. The electron-injecting contact layer may also be called the cathode.

There is a continuing need for charge transport materials for use in electronic devices.

SUMMARY OF THE INVENTION

There is provided a compound having Formula I:

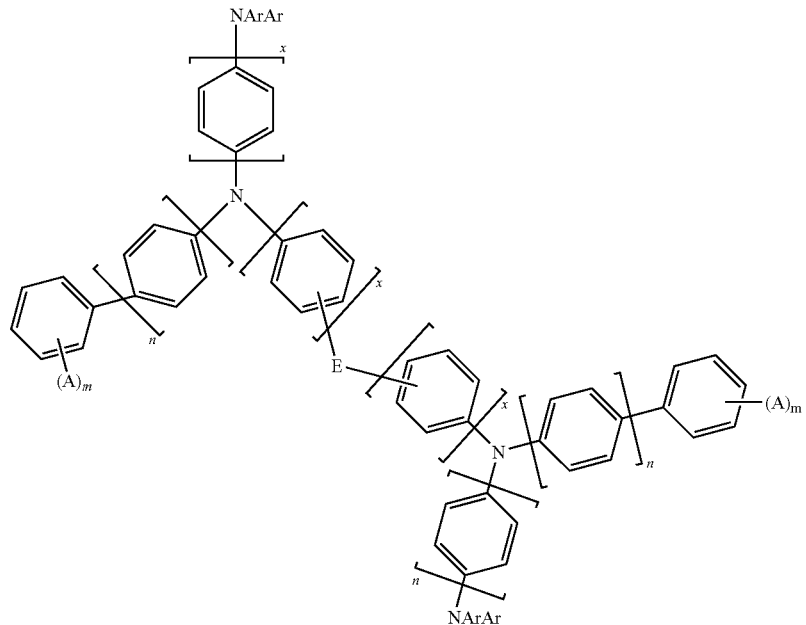

Formula I wherein:
Ar=aryl, heteroaryl, or Ar'—NAr'$_2$
Ar'=aryl, heteroaryl
A=H, D, Ar, —NAr$_2$, alkyl, heteroalkyl, fluoroalkyl, or Q
E=O, S, (SiR'R")$_n$, (CR'R")$_n$, or combinations thereof, and can be different at each occurrence, wherein R' and R" are each independently selected from H, F, D, amide, alkyl, aryl, alkoxy, aryloxy, heteroalkyl, heteroaryl, fluoroalkyl, fluoroaryl, fluoroalkoxy, and fluoroaryloxy
Q=leaving group
m=0 to 5
n=0 to 20
x=1 to 20.

There is also provided a polymer having at least one monomeric unit derived from the compound of Formula I, wherein at least two A=Q. Further provided are Compound 1 and Compound 2, derived from Formula I. Also further provided are Polymer 1 and Polymer 2, derived from Formula I under the conditions herein described.

There is also provided an electronic device comprising at least one layer comprising a compound having Formula I, including Compounds 1 and 2, or a polymer having at least one monomeric unit derived from the compound of Formula I, wherein at least two A=Q, including Polymers 1 and 2. The at least one layer of the electronic device may be an organic layer, a photoactive layer, or a hole transport layer.

The foregoing general description and the following detailed description are exemplary and explanatory only and are not restrictive of the invention, as defined in the appended claims.

BRIEF DESCRIPTION OF THE FIGURES

Embodiments are illustrated in the accompanying figures to improve understanding of concepts as presented herein.

Figure 1:
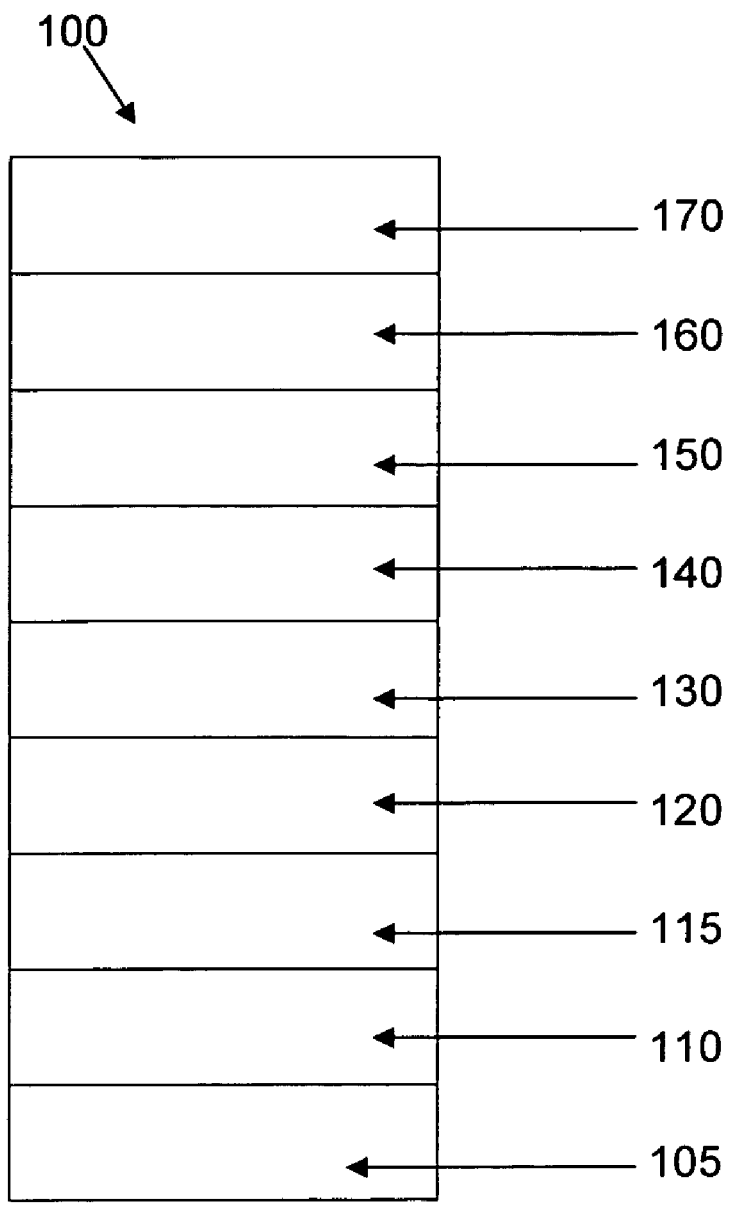
FIG. 1: An illustrative example of one organic electronic device comprising at least one layer comprising a novel compound or polymer as disclosed herein.
Figure 2:
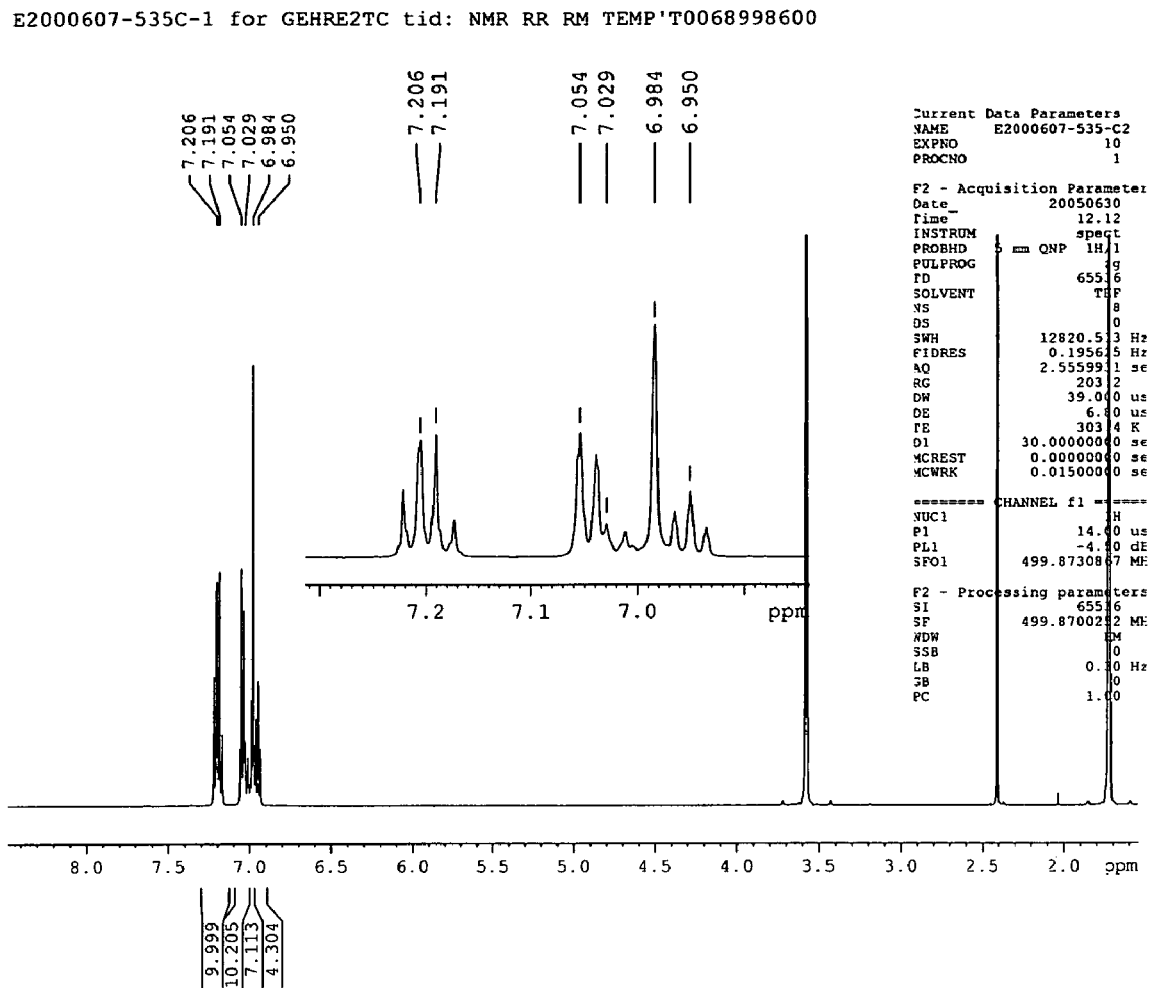
FIG. 2 is a 500 MHz $^1$H spectrum of Precursor 1.
Figure 3:
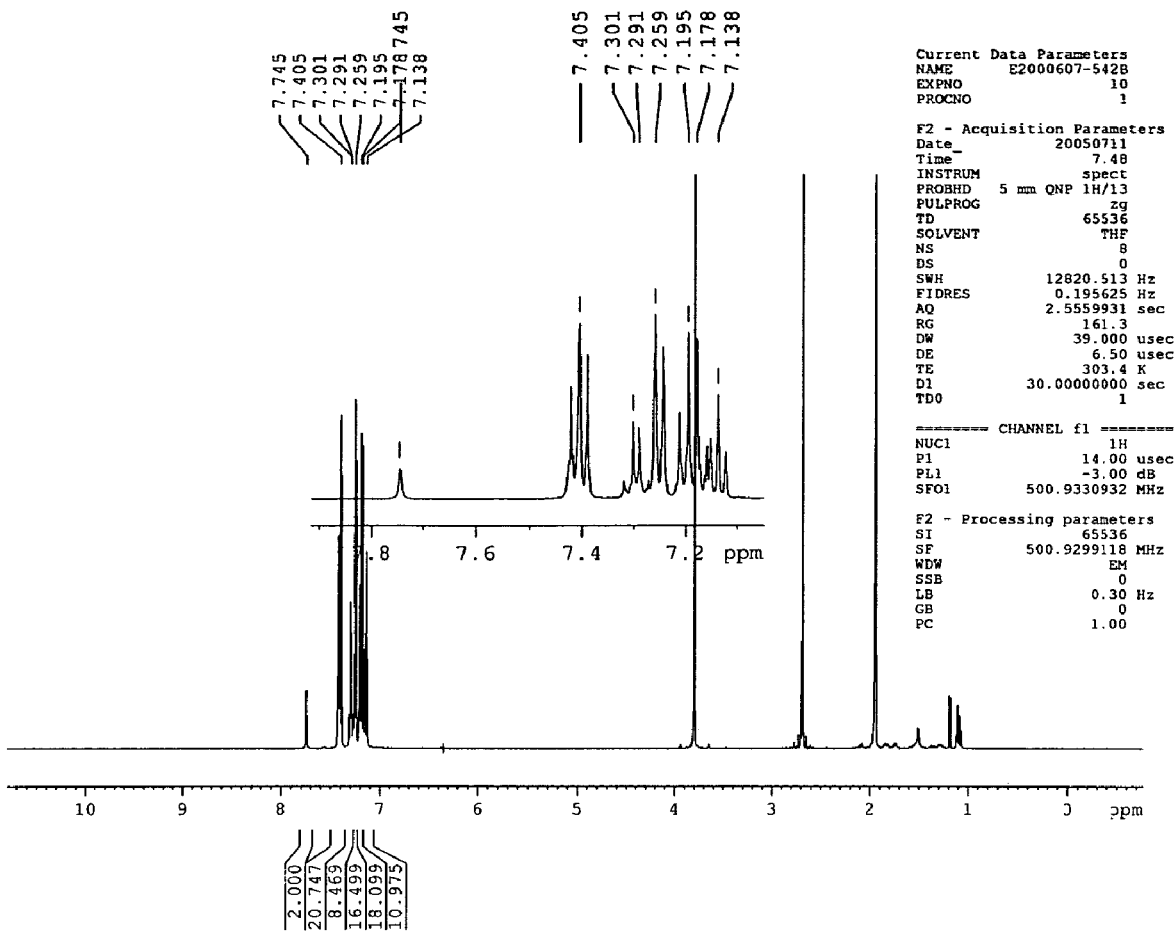
FIG. 3 is a 500 MHz $^1$H spectrum of Precursor 2.
Figure 4:
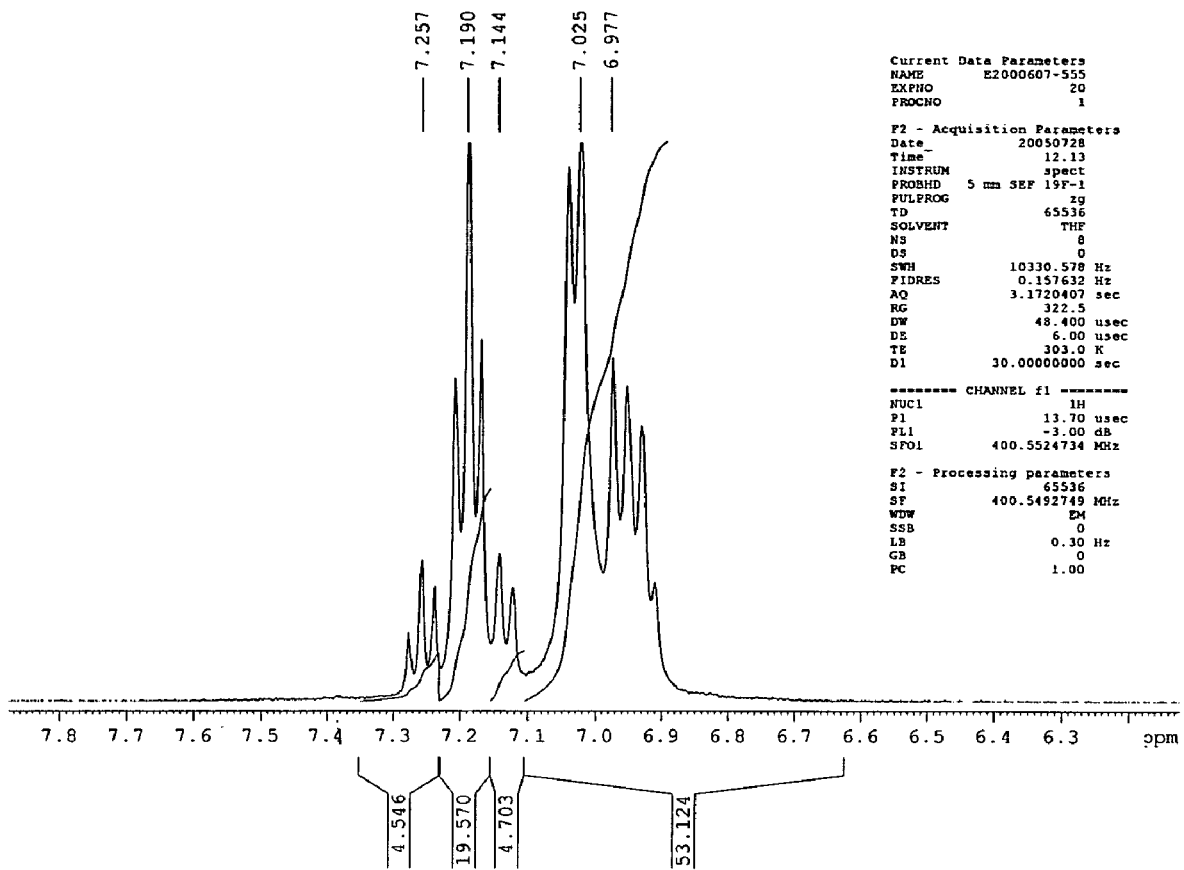
FIG. 4 is a 500 MHz $^1$H spectrum of Compound 2.
Figure 5:
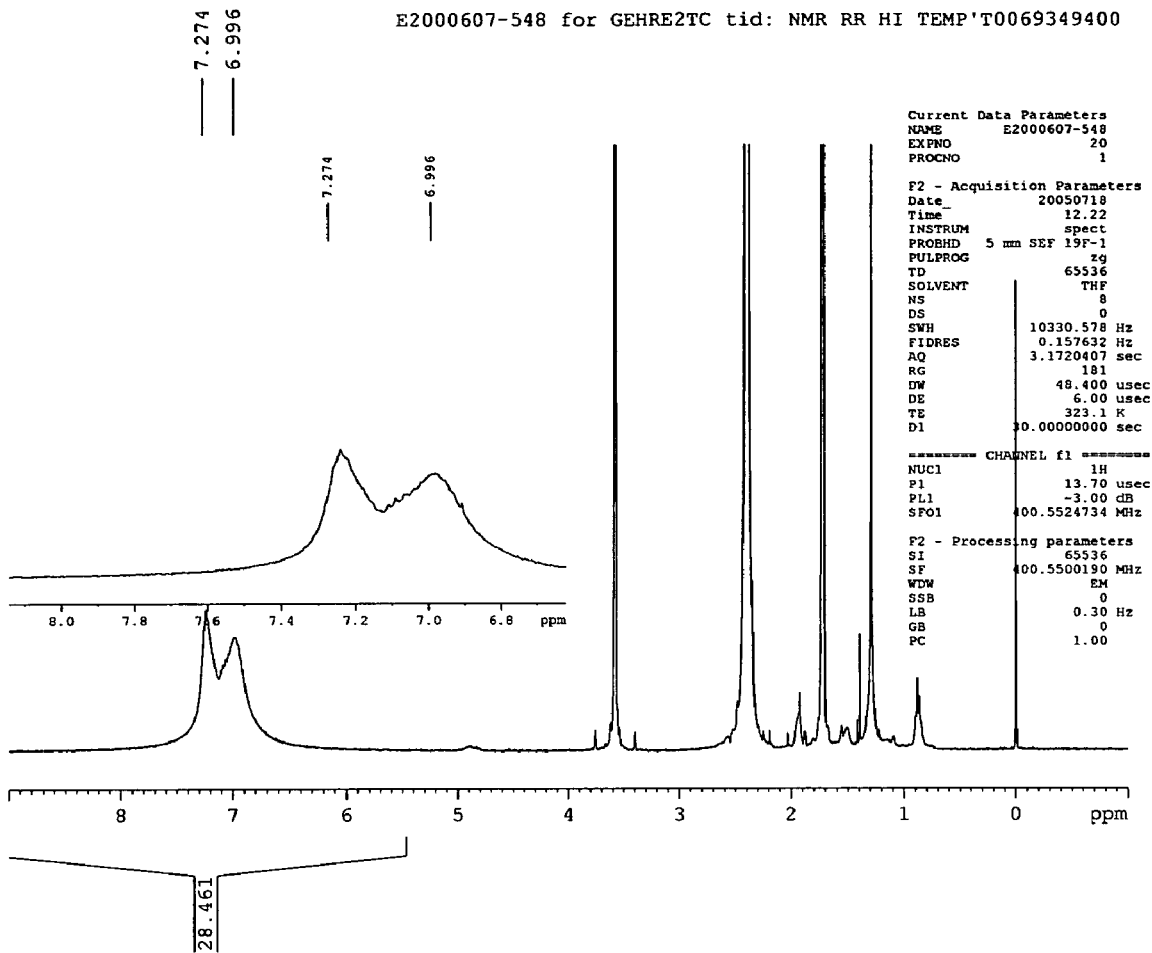
FIG. 5 is a 500 MHz $^1$H spectrum of Monomer 4.

Skilled artisans appreciate that objects in the figures are illustrated for simplicity and clarity and have not necessarily been drawn to scale. For example, the dimensions of some of the objects in the figures may be exaggerated relative to other objects to help to improve understanding of embodiments.

DETAILED DESCRIPTION

The compounds and polymers disclosed herein are useful in making hole transport layers for use in electronic devices. The hole transport layers can be used in any application wherein hole transport capacity is desired. In one embodiment, the compounds and polymers are useful as hosts for photoactive materials.

In the compounds and polymers, all A's, R's and Ar's are independently selected and may be the same or different.

The term "polymer" is intended to include oligomers, homopolymers, and copolymers having two or more different repeating units. Comonomers having the same structural repeat unit but different substituents would form a copolymer as that term is used herein. A polymer having repeating units derived from a monomer "X-T-X" will have repeating units -(T-)-.

The term "leaving group" is intended to mean a group that facilitates polymerization and is eliminated in the polymerization reaction. In one embodiment, the leaving group is a halide, triflate, boronic acid, boronic acid ester, or borane. In one embodiment, the leaving group is Cl or Br.

In one embodiment, the compound is Compound 1 or 2 below:

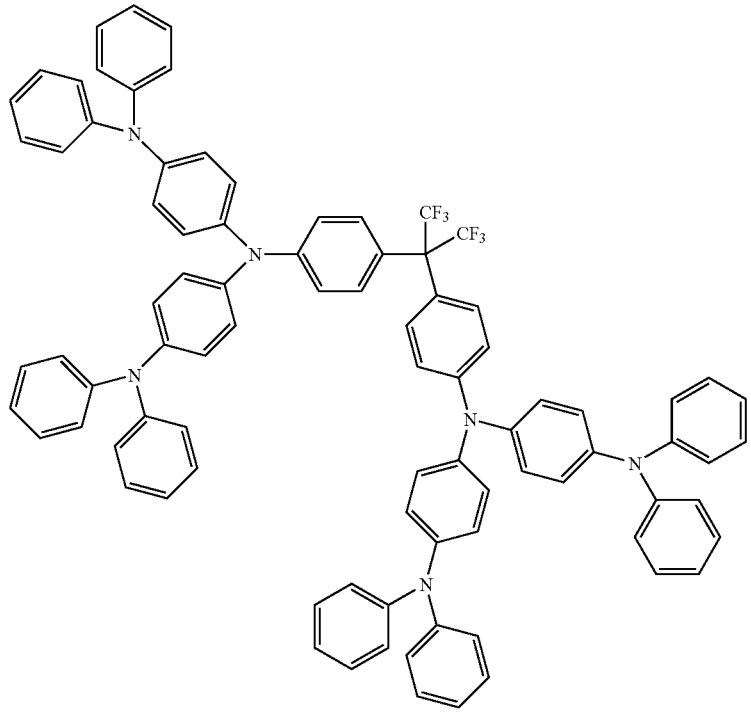

Compound 1

$C_{87}H_{64}F_6N_6$
Exact Mass: 1306.51
Mol. Wt: 1307.47

-continued
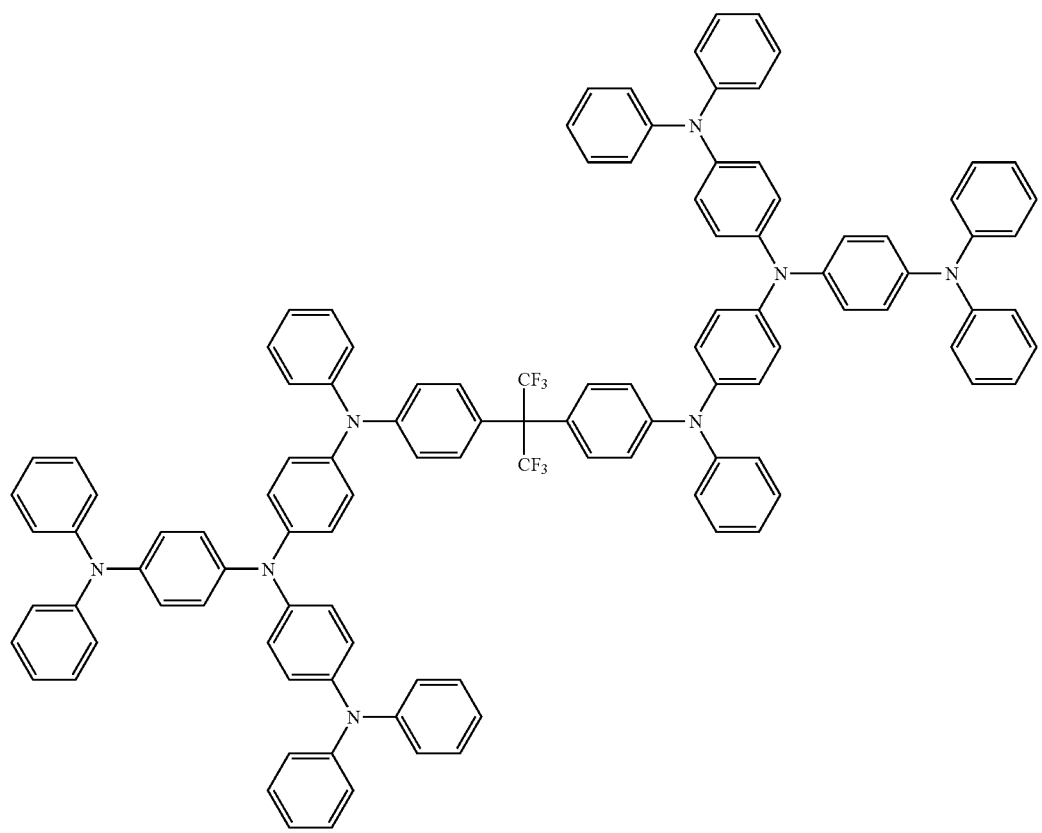
Compound 2
C₁₁₁H₈₂F₆N₈
Mol. Wt.: 1641.88
In one embodiment, the polymer is Polymer 1 or 2 below:
Polymer 1
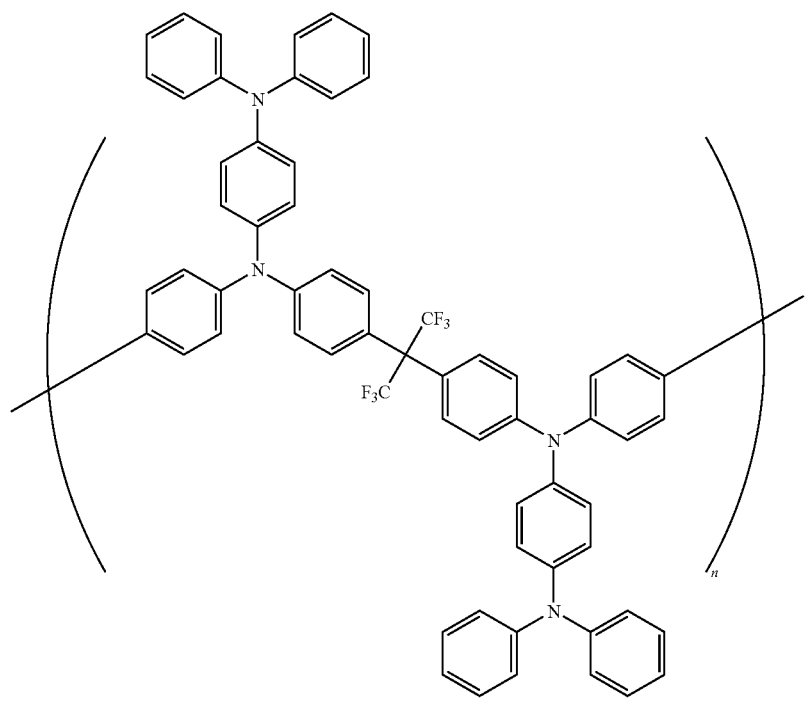

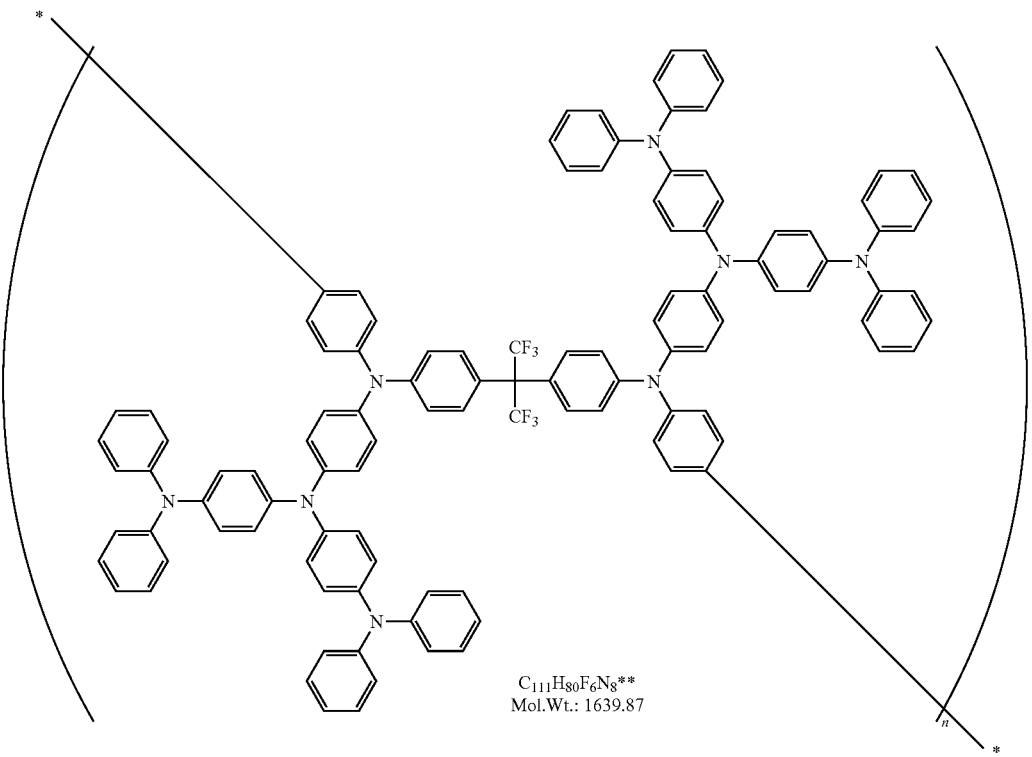

Polymer 2

C₁₁₁H₈₀F₆N₈**
Mol.Wt.: 1639.87

The compounds having Formula I can be made using known coupling reactions, as described in more detail in the examples.

The polymers as described herein can generally be prepared by three known synthetic routes. In a first synthetic method, as described in Yamamoto, Progress in Polymer Science, Vol. 17, p 1153 (1992), the dihalo derivatives of the monomeric units are reacted with a stoichiometric amount of a zerovalent nickel compound, such as bis(1,5-cyclooctadiene)nickel(0). In the second method, as described in Colon et al., Journal of Polymer Science, Part A, Polymer chemistry Edition, Vol. 28, p. 367 (1990). The dihalo derivatives of the monomeric units are reacted with catalytic amounts of Ni(II) compounds in the presence of stoichiometric amounts of a material capable of reducing the divalent nickel ion to zerovalent nickel. Suitable materials include zinc, magnesium, calcium and lithium. In the third synthetic method, as described in U.S. Pat. No. 5,962,631, and published PCT application WO 00/53565, a dihalo derivative of one monomeric unit is reacted with a derivative of another monomeric unit having two reactive groups selected from boronic acid, boronic acid esters, and boranes, in the presence of a zerovalent palladium catalyst, such as tetrakis(triphenylphosphine)Pd.

When the polymer described herein is a copolymer, it can be a random or block copolymer. Monomers may be reacted to form larger monomeric units which are then polymerized alone or with other monomers. A copolymer $-(AB)_x-(B)_y-$ may be formed by copolymerizing monomer X-A-X with monomer X-B-X, or by forming larger monomer X-A-B-X and polymerizing that monomer. In both cases, the resulting polymer is considered a copolymer derived from monomer X-A-X and monomer X-B-X.

In one embodiment, the polymer is a homopolymer. In one embodiment, the polymer is a copolymer having two or more monomeric units derived from compounds having Formula I. In one embodiment, the polymer is a copolymer having at least one monomeric unit derived from a compound having Formula I, and at least one monomeric unit derived from a second monomer. The second monomer can be a conjugated compound. Examples of conjugated compounds include, but are not limited to, arylenes, thiophenes, bithiophenes, arylenevinylenes, fluorenes, bifluorenes and dibenzosiloles, all of which may be substituted or unsubstituted.

The practical upper limit to the number of monomeric units in the polymer is determined in part by the desired solubility of a polymer in a particular solvent or class of solvents. As the number of monomeric units increases, the molecular weight of the compound increases. The increase in molecular weight is generally expected to result in a reduced solubility of the compound in a particular solvent. Moreover, in one embodiment, the number of moneric units at which a polymer becomes substantially insoluble in a given solvent is dependent in part upon the structure of the compound. For example, a compound containing multiple phenyl groups may become substantially insoluble in an organic solvent when number of monomeric units is much less than about $10^4$. As another example, a compound containing fewer phenyl groups and/or phenyl groups with particular functional groups may be soluble in a given solvent even though the number of monomeric units is about $10^4$ or greater, even $10^5$ or $10^6$. The selection of polymer molecular weight and a solvent is within the purview of one skilled in the art.

In one embodiment, there is provided a liquid composition comprising a compound having Formula I. In one embodiment, there is provided a liquid composition comprising a polymer having monomeric units derived from a compound having Formula I. The liquid composition may further comprise a photoactive material. The liquid composition can be in the form of, for example, a solution, dispersion, or emulsion.

In one embodiment, there is provided a process for making an organic electronic device. The process includes: providing a liquid composition comprising a compound having Formula I, or a polymer having monomeric units derived from a compound having Formula I; providing an anode; contacting said liquid comprising said compound with said anode; removing said liquid from said compound to produce a hole transport film; providing a photoactive material; disposing said photoactive material adjacent to said hole transport film; providing an electron transporter and disposing said electron transporter adjacent to said photoactive material; and providing a cathode adjacent to said electron transporter. The liquid can be, for example, a solution or dispersion. In one embodiment, a buffer layer is provided between the anode and the hole transport film.

In one embodiment, the process includes: providing a liquid composition comprising a photoactive compound and a compound having Formula I, or a polymer having monomeric units derived from a compound having Formula I; providing an anode; providing a hole transport material; disposing said hole transport material adjacent to said anode to form a hole transport film; contacting said liquid composition with said hole transport film; removing said liquid from said composition to produce a photoactive film comprising the photoactive material and a compound having Formula I or a polymer having at least one monomeric unit derived from a compound having Formula I providing an electron transporter and disposing said electron transporter adjacent to said photoactive film; and providing a cathode adjacent to said electron transporter. The liquid can be, for example, a solution or dispersion. In one embodiment, a buffer layer is provided between the anode and the hole transport film.

The term "organic electronic device" is intended to mean a device including one or more organic semiconductor layers or materials. An organic electronic device includes, but is not limited to: (1) a device that converts electrical energy into radiation (e.g., a light-emitting diode, light emitting diode display, diode laser, or lighting panel), (2) a device that detects a signal using an electronic process (e.g., a photodetector, a photoconductive cell, a photoresistor, a photoswitch, a phototransistor, a phototube, an infrared ("IR") detector, or a biosensors), (3) a device that converts radiation into electrical energy (e.g., a photovoltaic device or solar cell), (4) a device that includes one or more electronic components that include one or more organic semiconductor layers (e.g., a transistor or diode), or any combination of devices in items (1) through (4).

For making electronic devices, including OLED devices, in one embodiment, the compounds form films when deposited onto a transparent anode such as indium-doped tin oxide (ITO). The quality of the resultant film can be superficially judged by visual/microscopic inspection for smoothness and defect density. With respect to OLEDs, it is preferred that visually observed defects be minimal. Furthermore, film quality can be measured by estimation of film thickness over several separate areas of the film using, for example, an optical ellipsometer or a mechanical profilometer; it is preferred that the films have substantially uniform thicknesses as measured in the different areas of the film.

The liquid is preferably a solvent for the compound or polymer. A preferred solvent for a particular compound or related class of compounds can be readily determined by one skilled in the art. For some applications, it is preferred that the compounds be dissolved in non-aqueous solvents. Such non-aqueous solvents can be relatively polar, such as $C_1$ to $C_{20}$ alcohols, ethers, and acid esters, or can be relatively non-polar such as $C_1$ to $C_{12}$ alkanes or aromatics.

Other suitable liquids for use in making the liquid composition, either as a solution or dispersion as described herein, comprising the new compounds or polymers, include, but are not limited to, chlorinated hydrocarbons (such as methylene chloride, chloroform, chlorobenzene), aromatic hydrocarbons (such as substituted and non-substituted toluenes and xylenes), including triflurotoluene), polar solvents (such as tetrahydrofuran (THP), N-methyl pyrrolidone) esters (such as ethylacetate) alcohols (isopropanol), ketones (cyclopentatone) and mixtures thereof.

In one embodiment, the compound or polymer is dissolved in a solvent in which the compound is substantially soluble. The solution is then formed into a thin film and dried by any of several techniques such as spin-depositing, inkjetting etc. The resultant film formed as the solvent evaporates is then further dried by baking at elevated temperatures, including above the boiling point of the solvent, either in a vacuum of nitrogen atmosphere. The film is then subjected to further processing by depositing a second solution containing emissive layer materials on top of the pre-formed compound film where the emissive materials are dissolved in a solvent in which the compound is substantially insoluble. By "substantially insoluble" is meant that less than about 5 mg of the compound dissolves in 1 ml of the solvent. However, solubilities greater than or less than 5 mg can be used and may be preferred for some applications. For example, a modest solubility up to 10 mg/mL may result in a blurred or graded interface between the HTM copolymer described herein and the emissive layer materials. Such blurring can have deleterious or beneficial effects depending upon the natures of the materials involved. Such blurring of the interface can result in improved charge transport across the interface and substantially improved device performance or lifetime.

As will be recognized by one skilled in the art, the solubility of a compound is determined in part by substituent groups within the compound. In one embodiment, the compounds have a relatively low solubility, e.g., a solubility less than about 5 mg/mL, even about 2 mg/mL or less, in solvents that can be used to deposit an emissive layer film onto an electrode, which is typically a transparent anode such as ITO (indium doped tin oxide).

Device

There are also provided organic electronic devices comprising at least one layer containing a compound having Formula I or a polymer having at least one monomeric unit derived from a compound having Formula I, as a hole transport layer. Turning to FIG. 1, an exemplary organic electronic device 100 is shown. The device 100 includes a substrate 105. The substrate 105 may be rigid or flexible, inorganic or organic, for example, glass, ceramic, metal, or plastic. When voltage is applied, emitted light is visible through the substrate 105.

A first electrical contact layer 110 is deposited on the substrate 105. For illustrative purposes, the layer 110 is an anode layer. The anode layer may be deposited as lines, and is an electrode that is effective for injecting positive charge carriers. The anode can be made of, for example, materials containing or comprising metal, mixed metals, alloy, metal oxides or mixed-metal oxide. The anode may comprise a conducting polymer, polymer blend or polymer mixtures. Suitable metals include the Group 11 metals, the metals in Groups 4, 5, and 6, and the Group 8-10 transition metals. If the anode is to be light-transmitting, mixed-metal oxides of Groups 12, 13 and 14 metals, such as indium-tin-oxide, are generally used. The anode may also comprise an organic material, especially a conducting polymer such as polyaniline, including exemplary materials as described in "Flexible light-emitting diodes made from soluble conducting polymer," Nature vol. 357, pp 477 479 (11 Jun. 1992). At least one of the anode and cathode should be at least partially transparent to allow the generated light to be observed.

An optional buffer layer 115, such as hole transport materials, may be deposited over the anode layer 110, the latter being sometimes referred to as the "hole-injecting contact layer". The buffer layer can comprise hole transport materials. Examples of hole transport materials for layer 115 have been summarized, for example, in Kirk Othmer Encyclopedia of Chemical Technology, Fourth Edition, Vol. 18, p. 837 860, 1996, by Y. Wang. Both hole transporting "small" molecules as well as oligomers and polymers may be used. Hole transporting molecules include, but are not limited to: 4,4',4"-tris(N,N-diphenyl-amino)-triphenylamine (TDATA); 4,4',4"-tris(N-3-methylphenyl-N-phenyl-amino)-triphenylamine (MTDATA); N,N'-diphenyl-N,N'-bis(3-methylphenyl)-[1,1'-biphenyl]4,4'-diamine (TPD); 1,1-bis[(di4-tolylamino) phenyl]cyclohexane (TAPC); N,N'-bis(4-methylphenyl)-N,N'-bis(4-ethylphenyl)-[1,1'-(3,3'-dimethyl)biphenyl]4,4'-diamine (ETPD); tetrakis-(3-methylphenyl)-N,N,N',N'-2,5-phenylenediamine (PDA); α-phenyl-4-N,N-diphenylaminostyrene (TPS); p-(diethylamino)benzaldehyde diphenylhydrazone (DEH); triphenylamine (TPA); bis[4-(N,N-diethylamino)-2-methylphenyl](4-methylphenyl)methane (MPMP); 1-phenyl-3-[p-(diethylamino)styryl]-5-[p-(diethylamino)phenyl]pyrazoline (PPR or DEASP); 1,2-trans-bis(9H-carbazol-9-yl)cyclobutane (DCZB); N,N,N',N'-tetrakis(4-methylphenyl)-(1,1'-biphenyl)-4,4'-diamine (TTB); N,N'-bis(naphthalen-1-yl)-N,N'-bis-(phenyl)benzidine (α-NPB); 4,4'-N,N'-dicarbazolyl-biphenyl (CBP); and porphyrinic compounds, such as copper phthalocyanine. Useful hole transporting polymers include, but are not limited to, polyvinylcarbazole, (phenylmethyl)polysilane, polythiophene, polypyrrole, and polyaniline. The hole transporting polymer can be a complex of a conducting polymer and a colloid-forming polymeric acid, as disclosed in, published US applications US 2004/0254297 and US 2004/029133. Conducting polymers are useful as a class. It is also possible to obtain hole transporting polymers by doping hole transporting moieties, such as those mentioned above, into polymers such as polystyrenes and polycarbonates.

A hole transport layer 120 may be deposited over the buffer layer 115 when present, or over the first electrical contact layer 110. In one embodiment, the hole transport layer comprises a compound having Formula I or a polymer having at least one monomeric unit derived from a compound having Formula I, as described herein. In one embodiment, the hole transport layer comprises a different hole transport material. Any of the hole transport materials discussed above for the buffer layer 115 may be used in the hole transport layer 120.

An organic layer 130 may be deposited over the hole transport layer 120. In some embodiments, the organic layer 130 may be a number of discrete layers comprising a variety of components. Depending upon the application of the device, the organic layer 130 can be a light-emitting layer that is activated by an applied voltage (such as in a light-emitting diode or light-emitting electrochemical cell), or a layer of material that responds to radiant energy and generates a signal with or without an applied bias voltage (such as in a photodetector).

Other layers in the device can be made of any materials which are known to be useful in such layers upon consideration of the function to be served by such layers.

Any organic electroluminescent ("EL") material can be used as a photoactive material, e.g. in layer 130. Such materials include, but are not limited to, fluorescent dyes, small molecule organic fluorescent compounds, fluorescent and phosphorescent metal complexes, conjugated polymers, and mixtures thereof. Examples of fluorescent dyes include, but are not limited to, pyrene, perylene, rubrene, derivatives thereof, and mixtures thereof. Examples of metal complexes include, but are not limited to, metal chelated oxinoid compounds, such as tris(8-hydroxyquinolinato)aluminum (Alq3); cyclometalated iridium and platinum electroluminescent compounds, such as complexes of Iridium with phenylpyridine, phenylquinoline, or phenylpyrimidine ligands as disclosed in Petrov et al., Published PCT Application WO 02/02714, and organometallic complexes described in, for example, published applications US 2001/0019782, EP 1191612, WO 02/15645, and EP 1191614; and mixtures thereof. Electroluminescent emissive layers comprising a charge carrying host material and a metal complex have been described by Thompson et al., in U.S. Pat. No. 6,303,238, and by Burrows and Thompson in published PCT applications WO 00/70655 and WO 01/41512. Examples of conjugated polymers include, but are not limited to poly(phenylenevinylenes), polyfluorenes, poly(spirobifluorenes), polythiophenes, poly(p-phenylenes), copolymers thereof, and mixtures thereof.

In one embodiment of the device, photoactive material can be an organometallic complex. In another embodiment, the photoactive material is a cyclometalated complex of iridium or platinum. Other useful photoactive materials may be employed as well. Complexes of iridium with phenylpyridine, phenylquinoline, or phenylpyrimidine ligands have been disclosed as electroluminescent compounds in Petrov et al., Published PCT Application WO 02/02714. Other organometallic complexes have been described in, for example, published applications US 2001/0019782, EP 1191612, WO 02/15645, and EP 1191614. Electroluminescent devices with an active layer of polyvinyl carbazole (PVK) doped with metallic complexes of iridium have been described by Burrows and Thompson in published PCT applications WO 00/70655 and WO 01/41512. Electroluminescent emissive layers comprising a charge carrying host material and a phosphorescent platinum complex have been described by Thompson et al., in U.S. Pat. No. 6,303,238, Bradley et al., in Synth. Met. (2001), 116 (1-3), 379-383, and Campbell et al., in Phys. Rev. B, Vol. 65 085210.

In one embodiment, the photoactive layer 130 comprises a compound having Formula I or a polymer having at least one monomeric unit derived from a compound having Formula I, as a host for an electroluminescent material.

A second electrical contact layer 160 is deposited on the organic layer 130. For illustrative purposes, the layer 160 is a cathode layer.

Cathode layers may be deposited as lines or as a film. The cathode can be any metal or nonmetal having a lower work function than the anode. Exemplary materials for the cathode can include alkali metals of Group 1, especially lithium, the Group 2 (alkaline earth) metals, the Group 12 metals, including the rare earth elements and lanthanides, and the actinides. Materials such as aluminum, indium, calcium, barium, samarium and magnesium, as well as combinations, can be used. Li-containing and other compounds, such as LiF and $Li_2O$, may also be deposited between an organic layer and the cathode layer to lower the operating voltage of the system.

An electron transport layer 140 or electron injection layer 150 is optionally disposed adjacent to the cathode, the cathode being sometimes referred to as the "electron-injecting contact layer."

An encapsulation layer 170 is deposited over the contact layer 160 to prevent entry of undesirable components, such as water and oxygen, into the device 100. Such components can have a deleterious effect on the organic layer 130. In one embodiment, the encapsulation layer 170 is a barrier layer or film.

Though not depicted, it is understood that the device 100 may comprise additional layers. For example, there can be an additional layer (not shown) between the anode 110 and hole transport layer 120 to facilitate positive charge transport and/or band-gap matching of the layers, or to function as a protective layer. Other layers that are known in the art or otherwise may be used. In addition, any of the above-described layers may comprise two or more sub-layers or may form a laminar structure. Alternatively, some or all of anode layer 110, the hole transport layer 120, the electron transport layers 140 and 150, cathode layer 160, and other layers may be treated, especially surface treated, to increase charge carrier transport efficiency or other physical properties of the devices. The choice of materials for each of the component layers is preferably determined by balancing the goals of providing a device with high device efficiency with device operational lifetime considerations, fabrication time and complexity factors and other considerations appreciated by persons skilled in the art. It will be appreciated that determining optimal components, component configurations, and compositional identities would be routine to those of ordinary skill of in the art.

In one embodiment, the different layers have the following range of thicknesses: anode 110, 500-5000 Å, in one embodiment 1000-2000 Å; optional buffer layer 115 and hole transport layer 120, each 50-2000 Å, in one embodiment 200-1000 Å; photoactive layer 130, 10-2000 Å, in one embodiment 100-1000 Å; layers 140 and 150, each 50-2000 Å, in one embodiment 100-1000 Å; cathode 160, 200-10000 Å, in one embodiment 300-5000 Å. The location of the electron-hole recombination zone in the device, and thus the emission spectrum of the device, can be affected by the relative thickness of each layer. Thus the thickness of the electron-transport layer should be chosen so that the electron-hole recombination zone is in the light-emitting layer. The desired ratio of layer thicknesses will depend on the exact nature of the materials used.

In one embodiment, the device has the following structure, in order: anode, buffer layer, hole transport layer, photoactive layer, electron transport layer, electron injection layer, cathode. In one embodiment, the anode is made of indium tin oxide or indium zinc oxide. In one embodiment, the buffer layer comprises a conducting polymer selected from the group consisting of polythiophenes, polyanilines, polypyrroles, copolymers thereof, and mixtures thereof. In one embodiment, the buffer layer comprises a complex of a conducting polymer and a colloid-forming polymeric acid. In one embodiment, the buffer layer comprises a compound having triarylamine or triarylmethane groups. In one embodiment, the buffer layer comprises a material selected from the group consisting of TPD, MPMP, NPB, CBP, and mixtures thereof, as defined above.

In one embodiment, the hole transport layer comprises a compound having Formula I or a polymer having at least one monomeric unit derived from a compound having Formula I, as described herein.

In one embodiment, the photoactive layer comprises an electroluminescent metal complex and a host material. The host can be a charge transport material. In one embodiment, the host material is an organometallic complex having two or more 8-hydroxyquinolate ligands. In one embodiment, the host is a compound having Formula I or a polymer having at least one monomeric unit derived from a compound having Formula I, as described herein. In one embodiment, the electroluminescent complex is present in an amount of at least 1% by weight. In one embodiment, the electroluminescent complex is 2-20% by weight. In one embodiment, the electroluminescent complex is 20-50% by weight. In one embodiment, the electroluminescent complex is 50-80% by weight. In one embodiment, the electroluminescent complex is 80-99% by weight. In one embodiment, the metal complex is a cyclometalated complex of iridium, platinum, rhenium, or osmium. In one embodiment, the photoactive layer further comprises a second host material. The second host can be a charge transport material. In one embodiment, the second host is a hole transport material. In one embodiment, the second host is an electron transport material. In one embodiment, the second host material is a metal complex of a hydroxyaryl-N-heterocycle. In one embodiment, the hydroxyaryl-N-heterocycle is unsubstituted or substituted 8-hydroxyquinoline. In one embodiment, the metal is aluminum. In one embodiment, the second host is a material selected from the group consisting of tris(8-hydroxyquinolinato)aluminum, bis(8-hydroxyquinolinato) (4-phenylphenolato)aluminum, tetrakis(8-hydroxyquinolinato)zirconium, and mixtures thereof. The ratio of the first host to the second host can be 1:100 to 100:1. In one embodiment the ratio is from 1:10 to 10:1. In one embodiment, the ratio is from 1:10 to 1:5. In one embodiment, the ratio is from 1:5 to 1:1. In one embodiment, the ratio is from 1:1 to 5:1. In one embodiment, the ratio is from 5:1 to 5:10.

In one embodiment, the electron transport layer comprises a metal complex of a hydroxyaryl-N-heterocycle. In one embodiment, the hydroxyaryl-N-heterocycle is unsubstituted or substituted 8-hydroxyquinoline. In one embodiment, the metal is aluminum. In one embodiment, the electron transport layer comprises a material selected from the group consisting of tris(8-hydroxyquinolinato)aluminum, bis(8-hydroxyquinolinato)(4-phenylphenolato)aluminum, tetrakis(8-hydroxyquinolinato)zirconium, and mixtures thereof. In one embodiment, the electron injection layer is BaO, LiF or $LiO_2$. In one embodiment, the cathode is Al or Ba/Al.

In one embodiment, the device is fabricated by liquid deposition of the buffer layer, the hole transport layer, and the photoactive layer, and by vapor deposition of the electron transport layer, the electron injection layer, and the cathode.

The buffer layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is selected from the group consisting of alcohols, ketones, cyclic ethers, and polyols. In one embodiment, the organic liquid is selected from dimethylacetamide ("DMAc"), N-methylpyrrolidone ("NMP"), dimethylformamide ("DMF"), ethylene glycol ("EG"), aliphatic alcohols, and mixtures thereof. The buffer material can be present in the liquid medium in an amount from 0.5 to 10 percent by weight. Other weight percentages of buffer material may be used depending upon the liquid medium. The buffer layer can be applied by any continuous or discontinuous liquid deposition technique. In one embodiment, the buffer layer is applied by spin coating. In one embodiment, the buffer layer is applied by ink jet printing. After liquid deposition, the liquid medium can be removed in air, in an inert atmosphere, or by vacuum, at room temperature or with heating. In one embodiment, the layer is heated to a temperature less than 275° C. In one embodiment, the heating temperature is between 100° C. and 275° C. In one embodiment, the heating temperature is between 100° C. and 120° C. In one embodiment, the heating temperature is between 120° C. and 140° C. In one embodiment, the heating temperature is between 140° C. and 160° C. In one embodiment, the heating temperature is between 160° C. and 180° C. In one embodiment, the heating temperature is between 180° C. and 200° C. In one embodiment, the heating temperature is between 200° C. and 220° C. In one embodiment, the heating temperature is between 190° C. and 220° C. In one embodiment, the heating temperature is between 220° C. and 240° C. In one embodiment, the heating temperature is between 240° C. and 260° C. In one embodiment, the heating temperature is between 260° C. and 275° C. The heating time is dependent upon the temperature, and is generally between 5 and 60 minutes. In one embodiment, the final layer thickness is between 5 and 200 nm. In one embodiment, the final layer thickness is between 5 and 40 nm. In one embodiment, the final layer thickness is between 40 and 80 nm. In one embodiment, the final layer thickness is between 80 and 120 nm. In one embodiment, the final layer thickness is between 120 and 160 nm. In one embodiment, the final layer thickness is between 160 and 200 nm.

The hole transport layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is an aromatic solvent. In one embodiment, the organic liquid is selected from chloroform, dichloromethane, toluene, xylene, anisole, and mixtures thereof. The hole transport material can be present in the liquid medium in a concentration of 0.2 to 2 percent by weight. Other weight percentages of hole transport material may be used depending upon the liquid medium. The hole transport layer can be applied by any continuous or discontinuous liquid deposition technique. In one embodiment, the hole transport layer is applied by spin coating. In one embodiment, the hole transport layer is applied by ink jet printing.

After liquid deposition, the liquid medium can be removed in air, in an inert atmosphere, or by vacuum, at room temperature or with heating. In one embodiment, the layer is heated to a temperature less than 275° C. In one embodiment, the heating temperature is between 170° C. and 275° C. In one embodiment, the heating temperature is between 170° C. and 200° C. In one embodiment, the heating temperature is between 190° C. and 220° C. In one embodiment, the heating temperature is between 210° C. and 240° C. In one embodiment, the heating temperature is between 230° C. and 270° C. The heating time is dependent upon the temperature, and is generally between 5 and 60 minutes. In one embodiment, the final layer thickness is between 5 and 50 nm. In one embodiment, the final layer thickness is between 5 and 15 nm. In one embodiment, the final layer thickness is between 15 and 25 nm. In one embodiment, the final layer thickness is between 25 and 35 nm. In one embodiment, the final layer thickness is between 35 and 50 nm.

The photoactive layer can be deposited from any liquid medium in which it is dissolved or dispersed and from which it will form a film. In one embodiment, the liquid medium consists essentially of one or more organic solvents. In one embodiment, the liquid medium consists essentially of water or water and an organic solvent. In one embodiment the organic solvent is an aromatic solvent. In one embodiment, the organic liquid is selected from chloroform, dichloromethane, toluene, anisole, and mixtures thereof. The photoactive material can be present in the liquid medium in a concentration of 0.2 to 2 percent by weight. Other weight percentages of photoactive material may be used depending upon the liquid medium. The photoactive layer can be applied by any continuous or discontinuous liquid deposition technique. In one embodiment, the photoactive layer is applied by spin coating. In one embodiment, the photoactive layer is applied by ink jet printing. After liquid deposition, the liquid medium can be removed in air, in an inert atmosphere, or by vacuum, at room temperature or with heating. In one embodiment, the deposited layer is heated to a temperature that is less than the Tg of the material having the lowest Tg. In one embodiment, the heating temperature is at least 10° C. less than the lowest Tg. In one embodiment, the heating temperature is at least 20° C. less than the lowest Tg. In one embodiment, the heating temperature is at least 30° C. less than the lowest Tg. In one embodiment, the heating temperature is between 50° C. and 150° C. In one embodiment, the heating temperature is between 50° C. and 75° C. In one embodiment, the heating temperature is between 75° C. and 100° C. In one embodiment, the heating temperature is between 100° C. and 125° C. In one embodiment, the heating temperature is between 125° C. and 150° C. The heating time is dependent upon the temperature, and is generally between 5 and 60 minutes. In one embodiment, the final layer thickness is between 25 and 100 nm. In one embodiment, the final layer thickness is between 25 and 40 nm. In one embodiment, the final layer thickness is between 40 and 65 nm. In one embodiment, the final layer thickness is between 65 and 80 nm. In one embodiment, the final layer thickness is between 80 and 100 nm.

The electron transport layer can be deposited by any vapor deposition method. In one embodiment, it is deposited by thermal evaporation under vacuum. In one embodiment, the final layer thickness is between 1 and 100 nm. In one embodiment, the final layer thickness is between 1 and 15 nm. In one embodiment, the final layer thickness is between 15 and 30 nm. In one embodiment, the final layer thickness is between 30 and 45 nm. In one embodiment, the final layer thickness is between 45 and 60 nm. In one embodiment, the final layer thickness is between 60 and 75 nm. In one embodiment, the final layer thickness is between 75 and 90 nm. In one embodiment, the final layer thickness is between 90 and 100 nm.

The electron injection layer can be deposited by any vapor deposition method. In one embodiment, it is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C. In one embodiment, the material is heated to a temperature in the range of 100° C. to 150° C. In one embodiment, the material is heated to a temperature in the range of 150° C. to 200° C. In one embodiment, the material is heated to a temperature in the range of 200° C. to 250° C. In one embodiment, the material is heated to a temperature in the range of 250° C. to 300° C. In one embodiment, the material is heated to a temperature in the range of 300° C. to 350° C. In one embodiment, the material is heated to a temperature in the range of 350° C. to 400° C. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 0.1 and 3 nm. In one embodiment, the final layer thickness is between 0.1 and 1 nm. In one embodiment, the final layer thickness is between 1 and 2 nm. In one embodiment, the final layer thickness is between 2 and 3 nm.

The cathode can be deposited by any vapor deposition method. In one embodiment, it is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C. In one embodiment, the material is heated to a temperature in the range of 100° C. to 150° C. In one embodiment, the material is heated to a temperature in the range of 150° C. to 200° C. In one embodiment, the material is heated to a temperature in the range of 200° C. to 250° C. In one embodiment, the material is heated to a temperature in the range of 250° C. to 300° C. In one embodiment, the material is heated to a temperature in the range of 300° C. to 350° C. In one embodiment, the material is heated to a temperature in the range of 350° C. to 400° C. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 10 and 10000 nm. In one embodiment, the final layer thickness is between 10 and 1000 nm. In one embodiment, the final layer thickness is between 10 and 50 nm. In one embodiment, the final layer thickness is between 50 and 100 nm. In one embodiment, the final layer thickness is between 100 and 200 nm. In one embodiment, the final layer thickness is between 200 and 300 nm. In one embodiment, the final layer thickness is between 300 and 400 nm. In one embodiment, the final layer thickness is between 400 and 500 nm. In one embodiment, the final layer thickness is between 500 and 600 nm. In one embodiment, the final layer thickness is between 600 and 700 nm. In one embodiment, the final layer thickness is between 700 and 800 nm. In one embodiment, the final layer thickness is between 800 and 900 nm. In one embodiment, the final layer thickness is between 900 and 1000 nm. In one embodiment, the final layer thickness is between 1000 and 2000 nm. In one embodiment, the final layer thickness is between 2000 and 3000 nm. In one embodiment, the final layer thickness is between 3000 and 4000 nm. In one embodiment, the final layer thickness is between 4000 and 5000 nm. In one embodiment, the final layer thickness is between 5000 and 6000 nm. In one embodiment, the final layer thickness is between 6000 and 7000 nm. In one embodiment, the final layer thickness is between 7000 and 8000 nm. In one embodiment, the final layer thickness is between 8000 and 9000 nm. In one embodiment, the final layer thickness is between 9000 and 10000 nm.

In one embodiment, the device is fabricated by vapor deposition of the buffer layer, the hole transport layer, and the photoactive layer, the electron transport layer, the electron injection layer, and the cathode.

In one embodiment, the buffer layer is applied by vapor deposition. In one embodiment, it is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C. In one embodiment, the material is heated to a temperature in the range of 100° C. to 150° C. In one embodiment, the material is heated to a temperature in the range of 150° C. to 200° C. In one embodiment, the material is heated to a temperature in the range of 200° C. to 250° C. In one embodiment, the material is heated to a temperature in the range of 250° C. to 300° C. In one embodiment, the material is heated to a temperature in the range of 300° C. to 350° C. In one embodiment, the material is heated to a temperature in the range of 350° C. to 400° C. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 5 and 200 nm. In one embodiment, the final layer thickness is between 5 and 30 nm. In one embodiment, the final layer thickness is between 30 and 60 nm. In one embodiment, the final layer thickness is between 60 and 90 nm. In one embodiment, the final layer thickness is between 90 and 120 nm. In one embodiment, the final layer thickness is between 120 and 150 nm. In one embodiment, the final layer thickness is between 150 and 280 nm. In one embodiment, the final layer thickness is between 180 and 200 nm.

In one embodiment, the hole transport layer is applied by vapor deposition. In one embodiment, it is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C. In one embodiment, the material is heated to a temperature in the range of 100° C. to 150° C. In one embodiment, the material is heated to a temperature in the range of 150° C. to 200° C. In one embodiment, the material is heated to a temperature in the range of 200° C. to 250° C. In one embodiment, the material is heated to a temperature in the range of 250° C. to 300° C. In one embodiment, the material is heated to a temperature in the range of 300° C. to 350° C. In one embodiment, the material is heated to a temperature in the range of 350° C. to 400° C. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 5 and 200 nm. In one embodiment, the final layer thickness is between 5 and 30 nm. In one embodiment, the final layer thickness is between 30 and 60 nm. In one embodiment, the final layer thickness is between 60 and 90 nm. In one embodiment, the final layer thickness is between 90 and 120 nm. In one embodiment, the final layer thickness is between 120 and 150 nm. In one embodiment, the final layer thickness is between 150 and 280 nm. In one embodiment, the final layer thickness is between 180 and 200 nm.

In one embodiment, the photoactive layer is applied by vapor deposition. In one embodiment, it is deposited by thermal evaporation under vacuum. In one embodiment, the photoactive layer consists essentially of a single electroluminescent compound, which is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C. In one embodiment, the material is heated to a temperature in the range of 100° C. to 150° C. In one embodiment, the material is heated to a temperature in the range of 150° C. to 200° C. In one embodiment, the material is heated to a temperature in the range of 200° C. to 250° C. In one embodiment, the material is heated to a temperature in the range of 250° C. to 300° C. In one embodiment, the material is heated to a temperature in the range of 300° C. to 350° C. In one embodiment, the material is heated to a temperature in the range of 350° C. to 400° C. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 5 and 200 nm. In one embodiment, the final layer thickness is between 5 and 30 nm. In one embodiment, the final layer thickness is between 30 and 60 nm. In one embodiment, the final layer thickness is between 60 and 90 nm. In one embodiment, the final layer thickness is between 90 and 120 nm. In one embodiment, the final layer thickness is between 120 and 150 nm. In one embodiment, the final layer thickness is between 150 and 280 nm. In one embodiment, the final layer thickness is between 180 and 200 nm.

In one embodiment, the photoactive layer comprises two electroluminescent materials, each of which is applied by thermal evaporation under vacuum. Any of the above listed vacuum conditions and temperatures can be used. Any of the above listed deposition rates can be used. The relative deposition rates can be from 50:1 to 1:50. In one embodiment, the relative deposition rates are from 1:1 to 1:3. In one embodiment, the relative deposition rates are from 1:3 to 1:5. In one embodiment, the relative deposition rates are from 1:5 to 1:8. In one embodiment, the relative deposition rates are from 1:8 to 1:10. In one embodiment, the relative deposition rates are from 1:10 to 1:20. In one embodiment, the relative deposition rates are from 1:20 to 1:30. In one embodiment, the relative deposition rates are from 1:30 to 1:50. The total thickness of the layer can be the same as that described above for a single-component photoactive layer.

In one embodiment, the photoactive layer comprises one electroluminescent material and at least one host material, each of which is applied by thermal evaporation under vacuum. Any of the above listed vacuum conditions and temperatures can be used. Any of the above listed deposition rates can be used. The relative deposition rate of electroluminescent material to host can be from 1:1 to 1:99. In one embodiment, the relative deposition rates are from 1:1 to 1:3. In one embodiment, the relative deposition rates are from 1:3 to 1:5. In one embodiment, the relative deposition rates are from 1:5 to 1:8. In one embodiment, the relative deposition rates are from 1:8 to 1:10. In one embodiment, the relative deposition rates are from 1:10 to 1:20. In one embodiment, the relative deposition rates are from 1:20 to 1:30. In one embodiment, the relative deposition rates are from 1:30 to 1:40. In one embodiment, the relative deposition rates are from 1:40 to 1:50. In one embodiment, the relative deposition rates are from 1:50 to 1:60. In one embodiment, the relative deposition rates are from 1:60 to 1:70. In one embodiment, the relative deposition rates are from 1:70 to 1:80. In one embodiment, the relative deposition rates are from 1:80 to 1:90. In one embodiment, the relative deposition rates are from 1:90 to 1:99. The total thickness of the layer can be the same as that described above for a single-component photoactive layer.

In one embodiment, the electron transport layer is applied by vapor deposition. In one embodiment, it is deposited by thermal evaporation under vacuum. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the vacuum is less than $10^{-6}$ torr. In one embodiment, the vacuum is less than $10^{-7}$ torr. In one embodiment, the vacuum is less than $10^{-8}$ torr. In one embodiment, the material is heated to a temperature in the range of 100° C. to 400° C. In one embodiment, the material is heated to a temperature in the range of 100° C. to 150° C. In one embodiment, the material is heated to a temperature in the range of 150° C. to 200° C. In one embodiment, the material is heated to a temperature in the range of 200° C. to 250° C. In one embodiment, the material is heated to a temperature in the range of 250° C. to 300° C. In one embodiment, the material is heated to a temperature in the range of 300° C. to 350° C. In one embodiment, the material is heated to a temperature in the range of 350° C. to 400° C. In one embodiment, the material is deposited at a rate of 0.5 to 10 Å/sec. In one embodiment, the material is deposited at a rate of 0.5 to 1 Å/sec. In one embodiment, the material is deposited at a rate of 1 to 2 Å/sec. In one embodiment, the material is deposited at a rate of 2 to 3 Å/sec. In one embodiment, the material is deposited at a rate of 3 to 4 Å/sec. In one embodiment, the material is deposited at a rate of 4 to 5 Å/sec. In one embodiment, the material is deposited at a rate of 5 to 6 Å/sec. In one embodiment, the material is deposited at a rate of 6 to 7 Å/sec. In one embodiment, the material is deposited at a rate of 7 to 8 Å/sec. In one embodiment, the material is deposited at a rate of 8 to 9 Å/sec. In one embodiment, the material is deposited at a rate of 9 to 10 Å/sec. In one embodiment, the final layer thickness is between 5 and 200 nm. In one embodiment, the final layer thickness is between 5 and 30 nm. In one embodiment, the final layer thickness is between 30 and 60 nm. In one embodiment, the final layer thickness is between 60 and 90 nm. In one embodiment, the final layer thickness is between 90 and 120 nm. In one embodiment, the final layer thickness is between 120 and 150 nm. In one embodiment, the final layer thickness is between 150 and 280 nm. In one embodiment, the final layer thickness is between 180 and 200 nm.

In one embodiment, the electron injection layer is applied by vapor deposition, as described above.

In one embodiment, the cathode is applied by vapor deposition, as describe above.

In one embodiment, the device is fabricated by vapor deposition of some of the organic layers, and liquid deposition of some of the organic layers. In one embodiment, the device is fabricated by liquid deposition of the buffer layer, and vapor deposition of all of the other layers.

In operation, a voltage from an appropriate power supply (not depicted) is applied to the device 100. Current therefore passes across the layers of the device 100. Electrons enter the organic polymer layer, releasing photons. In some OLEDs, called active matrix OLED displays, individual deposits of photoactive organic films may be independently excited by the passage of current, leading to individual pixels of light emission. In some OLEDs, called passive matrix OLED displays, deposits of photoactive organic films may be excited by rows and columns of electrical contact layers.

The devices can be prepared employing a variety of techniques. These include, by way of non-limiting exemplification, vapor deposition techniques and liquid deposition.

As used herein, the term "hole transport" when referring to a layer, material, member, or structure, is intended to mean such layer, material, member, or structure facilitates migration of positive charges through the thickness of such layer, material, member, or structure with relative efficiency and small loss of charge.

The term "composition", used alone to refer to compositions having particular formulas disclosed and claimed herein, is intended to be construed broadly to include the compounds, monomers, dimers, oligomers and polymers thereof, as well as solutions, dispersions, liquid and solid mixtures and admixtures.

The term "anti-quenching composition" is intended to mean a material which prevents, retards, or diminishes both the transfer of energy and the transfer of an electron to or from the excited state of the photoactive layer to an adjacent layer.

The term "photoactive" refers to any material that exhibits electroluminescence, photoluminescence, and/or photosensitivity.

The term "group" is intended to mean a part of a compound, such as a substituent in an organic compound. The prefix "hetero" indicates that one or more carbon atoms have been replaced with a different atom. The prefix "fluoro" indicates that one or more hydrogens have been replaced with a fluorine.

The term "alkyl" is intended to mean a group derived from an aliphatic hydrocarbon having one point of attachment, which group may be unsubstituted or substituted. In one embodiment, an alkyl group may have from 1-20 carbon atoms. The term "aryl" is intended to mean a group derived from an aromatic hydrocarbon having one point of attachment, which group may be unsubstituted or substituted. In one embodiment, an aryl group may have from 6-30 carbon atoms. In one embodiment, a heteroaryl group may have from 2-30 carbon atoms. The term "alkoxy" is intended to mean the group —OR, where R is alkyl, fluoroalkyl, or heteroalkyl. The term "aryloxy" is intended to mean the group —OR, where R is aryl or heteroaryl.

The term "amide" is intended to mean the group —C(O)NR2, where R is H, alkyl, fluoroalkyl, heteroalkyl, aryl, or heteroaryl.

The term "photoactive" is intended to mean to any material that exhibits electroluminescence or photosensitivity.

Unless otherwise indicated, all groups can be unsubstituted or substituted. The phrase "adjacent to," when used to refer to layers in a device, does not necessarily mean that one layer is immediately next to another layer. On the other hand, the phrase "adjacent R groups," is used to refer to R groups that are next to each other in a chemical formula (i.e., R groups that are on atoms joined by a bond).

The term "compound" is intended to mean an electrically uncharged substance made up of molecules that further consist of atoms, wherein the atoms cannot be separated by physical means.

The term "copolymer" is intended to encompass oligomeric species and include materials having 2 or more monomeric units. In addition, the IUPAC numbering system is used throughout, where the groups from the Periodic Table are numbered from left to right as 1 through 18 (CRC Handbook of Chemistry and Physics, $81^{st}$ Edition, 2000).

As used herein, "solution processing" means processes that include depositing from a liquid medium. The liquid medium can be in the form of a solution, a dispersion, an emulsion, or other forms.

The term "layer" is used interchangeably with the term "film" and refers to a coating covering a desired area. The term is not limited by size. The area can be as large as an entire device or as small as a specific functional area such as the actual visual display, or as small as a single sub-pixel. Layers and films can be formed by any conventional deposition technique, including vapor deposition, liquid deposition (continuous and discontinuous techniques), and thermal transfer. Continuous deposition techniques, include but are not limited to, spin coating, gravure coating, curtain coating, dip coating, slot-die coating, spray coating, and continuous nozzle coating. Discontinuous deposition techniques include, but are not limited to, ink jet printing, gravure printing, and screen printing.

As used herein, the terms "comprises," "comprising," "includes," "including," "has," "having" or any other variation thereof, are intended to cover a non-exclusive inclusion. For example, a process, method, article, or apparatus that comprises a list of elements is not necessarily limited to only those elements but may include other elements not expressly listed or inherent to such process, method, article, or apparatus. Further, unless expressly stated to the contrary, "or" refers to an inclusive or and not to an exclusive or. For example, a condition A or B is satisfied by any one of the following: A is true (or present) and B is false (or not present), A is false (or not present) and B is true (or present), and both A and B are true (or present).

Also, "the", "a" or "an" are employed to describe elements and components of the invention. This is done merely for convenience and to give a general sense of the invention. This description should be read to include one or at least one and the singular also includes the plural unless it is obvious that it is meant otherwise.

Unless otherwise defined, all technical and scientific terms used herein have the same meaning as commonly understood by one of ordinary skill in the art to which this invention belongs. Unless otherwise defined, all letter symbols in the figures represent atoms with that atomic abbreviation. Although methods and materials similar or equivalent to those described herein can be used in the practice or testing of the present invention, suitable methods and materials are described below.

All publications, patent applications, patents, and other references mentioned herein are incorporated by reference in their entirety. In case of conflict, the present specification, including definitions, will control. In addition, the materials, methods, and examples are illustrative only and not intended to be limiting.

EXAMPLES

The following examples illustrate certain features and advantages of the present invention. They are intended to be illustrative of the invention, but not limiting. All percentages are by weight, unless otherwise indicated.

Example 1

This example illustrates the synthesis of Compound 2.

Part 1. Synthesis of N,N-bis(p-diphenylamino)-4-chloroaniline, Precursor (1)

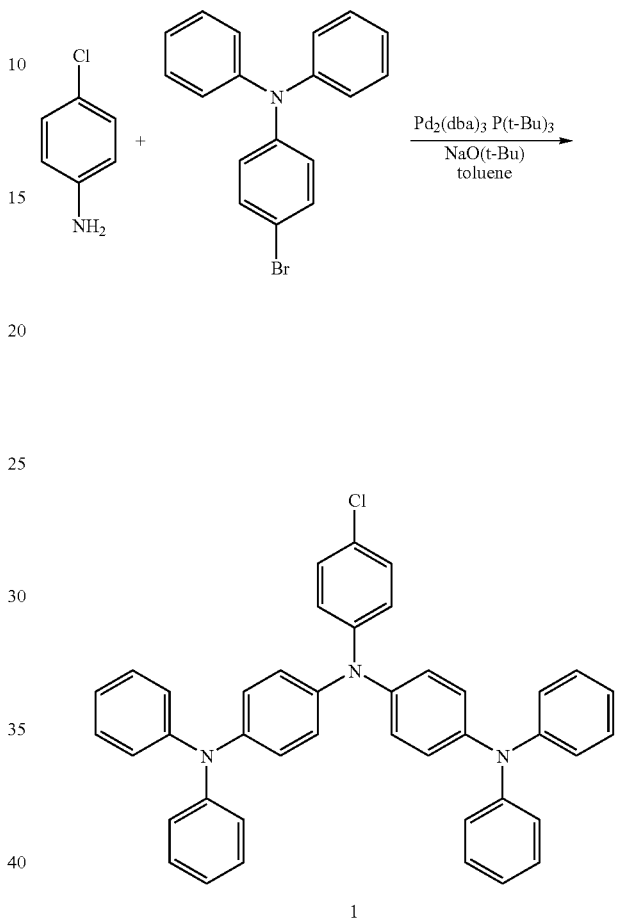

In a $N_2$ purged dry box, 4-chloroaniline (10 g, 78 mmol), 4-bromophenyl-N,N-diphenylaniline (63.5 g, 196 mmol) and toluene (380 ml) are combined in a 1 L round bottom flask equipped with a magnetic stirrer. Tri-t-butylphosphine (1.1 g, 5.4 mmol), tris(dibenzylideneacetone)dipalladium(0) (2.5 g, 2.7 mmol) and sodium t-butoxide (18.8 g, 196 mmol) are added. The reaction flask is capped and the contents are stirred at room temperature for 84 hours. The reaction is removed from the dry box and filtered through a pad of silica gel (100 g) topped with diatomaceous earth (250 g) and rinsed with toluene (1.5 L). The filtrate and rinse are combined and concentrated on the rotary evaporator. The residue is dried under high vacuum to give a greenish-brown solid (60 g). The product is purified by flash column chromatography (silica gel; 7.5%-30% $CH_2Cl_2$/hexanes gradient) to give 14.5 g nearly pure product. The product is stirred under $N_2$ in refluxing acetone (1.6 L), cooled to room temperature, isolated by vacuum filtration and rinsed with acetone. After drying under high vacuum, 9.3 g (19%) of pure product is obtained as a light green powder. $^1$H NMR spectrum (500 MHz, $CDCl_3$, TMS standard) is consistent with the structure of Precursor (1).

Part 2. Synthesis of Precursor (2)
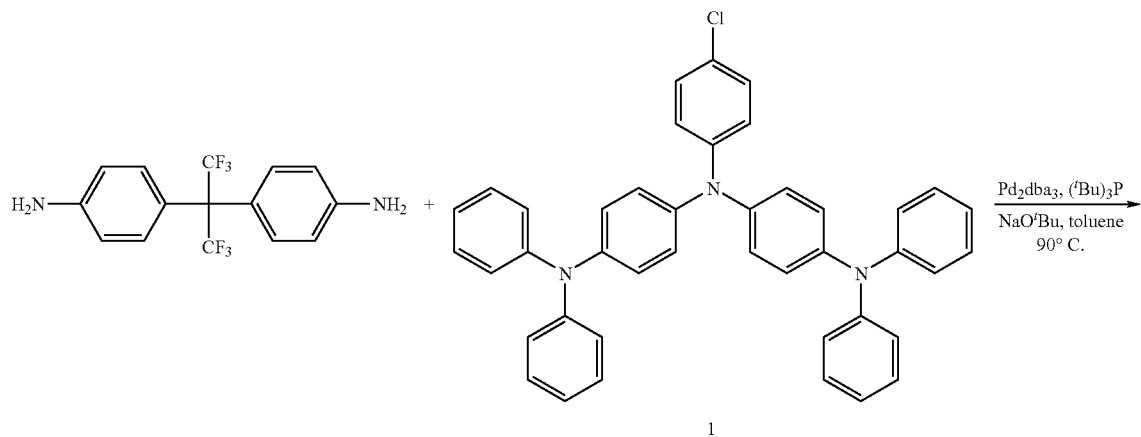
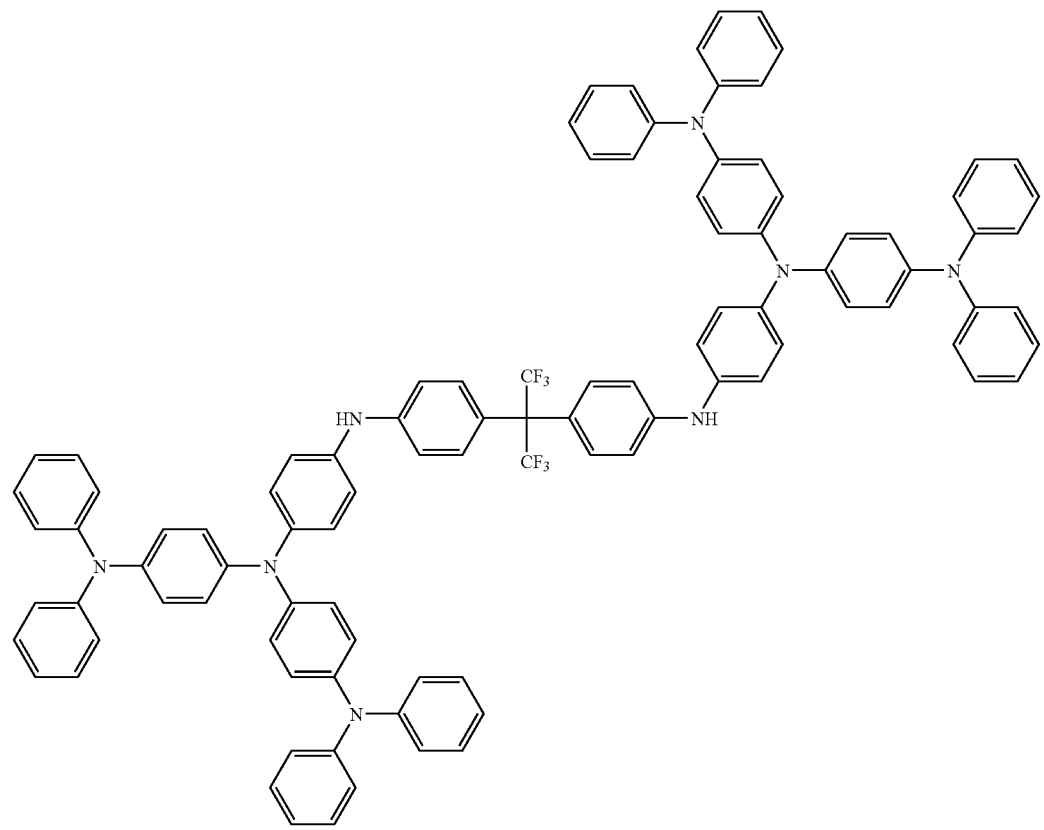

4,4'-(Hexafluoroisopropylidene)dianiline (2.6 g, 7.7 mmol) is dissolved in toluene (50 ml) in a 250 ml Schlenk vessel in a $N_2$ purged glovebox. N,N-Bis(p-diphenylamino)-4-chloroaniline, Precursor (1) (10.0 g, 16.3 mmol) and tri-t-butylphosphine (0.162 g, 0.800 mmol) are added. Tris(dibenzylideneacetone)dipalladium(0) (0.353 g, 0.400 mmol) and sodium-1-butoxide are added and rinsed in with toluene (50 ml). The reaction vessel is sealed, removed from the dry box and heated at 90° C. for 17 hours. The reaction is cooled to room temperature and filtered through a pad of silica gel (10 g) topped with diatomaceous earth (25 g), rinsing with toluene (800 ml). The combined filtrate and rinse are concentrated on a rotary evaporator under reduced pressure and dried under high vacuum to give a brownish orange semisolid. The product is purified by flash column chromatography (silica gel; 7:3-2/1 hexanes/$CH_2Cl_2$ gradient) to yield a light yellow solid (6.18 g). The obtained solid is further purified by flash column chromatography under the same conditions to give a yellow-green solid (6.0 g). The product is suspended in ethyl acetate (50 ml), stirred under $N_2$ for 24 hours, filtered, rinsed with ethyl acetate (20 ml) and dried under high vacuum to give 4.1 g of a light green solid (36%). 1H NMR spectrum (500 MHz, THF-$d_8$, TMS standard) is consistent with the structure of Precursor (2).

Part 3. Synthesis of Compound 2

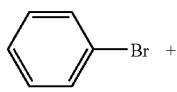

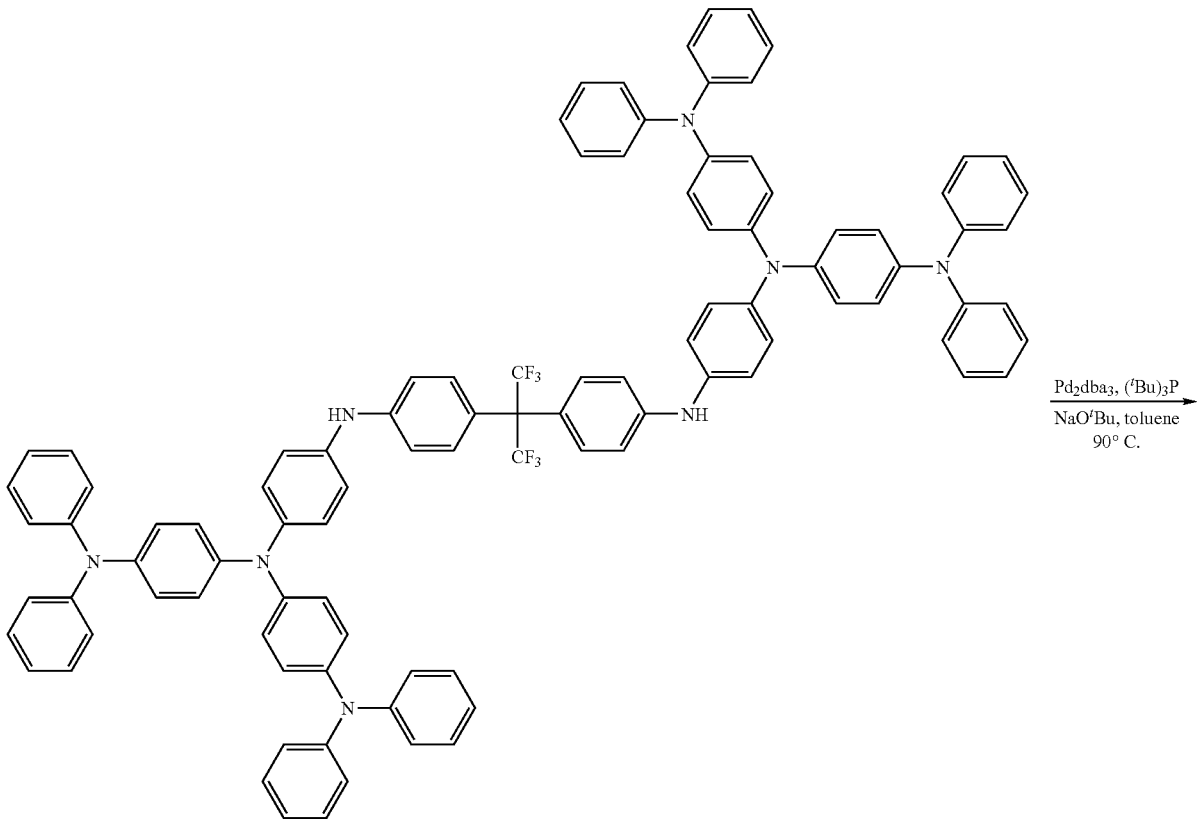

(2)

-continued

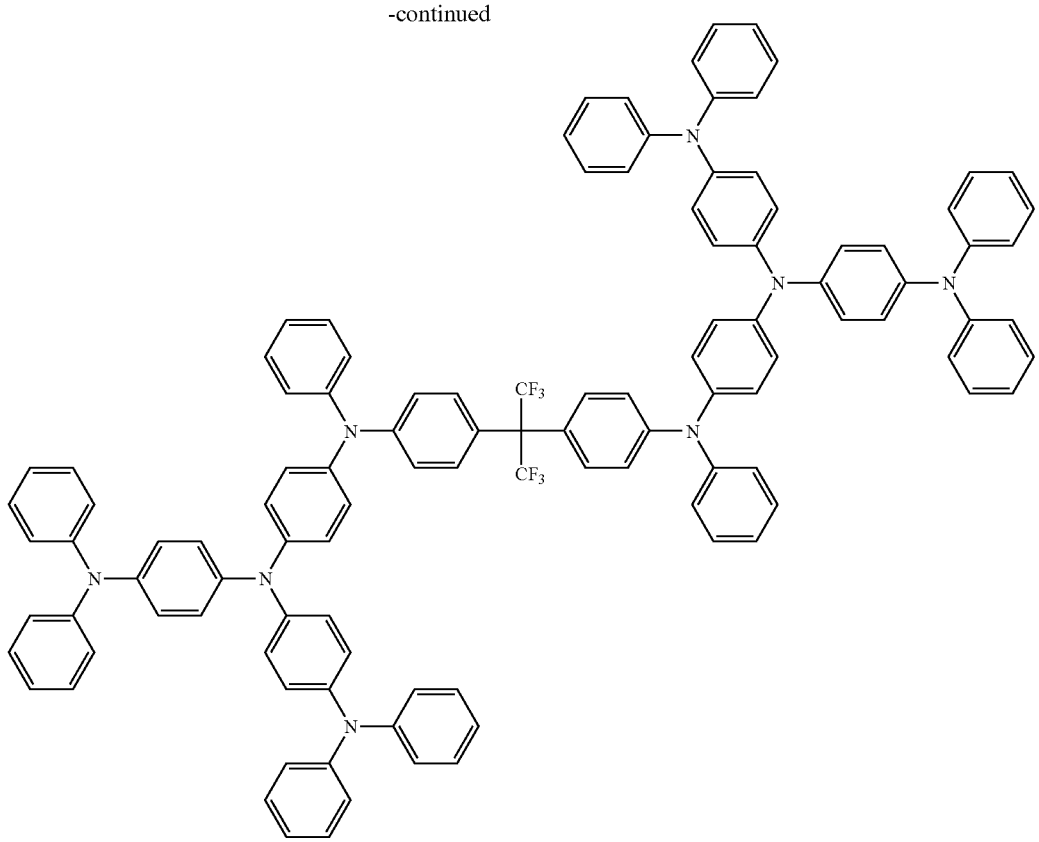
Compound 2

Glassware is pre-dried in an oven. Precursor (2) (1.0 g, 0.67 mmol) and bromobenzene (0.32 g, 2.0 mmol) are dissolved in toluene (4 ml). Tri-t-butylphosphine (0.014 g, 0.067 mmol) and tris(dibenzylideneacetone)dipalladium(0) (0.031 g, 0.034 mmol) and sodium t-butoxide (0.155 g, 1.6 mmol) are added. The reaction is capped and stirred at room temperature for 18.5 hours. The reaction is removed from the dry box, diluted with THF (20 ml) and filtered through a pad of silica gel (10 g) topped with diatomaceous earth (25 g). The filter is rinsed rinsing with THF (175 ml). The combined filtrate and rinse are concentrated on a rotary evaporator under reduced pressure and dried under high vacuum to give a brown oil. The oil is suspended in acetone (25 ml) and stirred for one hour. The product is isolated by filtration, rinsing with acetone (50 ml) to give a beige powder. The crude product is suspended in acetone and heated at reflux with stirring under $N_2$ for 20 minutes. The pure product is isolated by filtration while hot, rinsing with 5 ml acetone, and dried under high vacuum to give 0.99 g (90%) of a light yellow powder. The $^1$H NMR spectrum (500 MHz, THF-$d_8$, TMS standard) is consistent with the structure of Compound 2.

Compound 1 is made in an analogous manner.

Example 2

This example illustrates the synthesis of Polymer 2.
Part 1. Synthesis of Monomer (4)

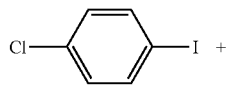

-continued
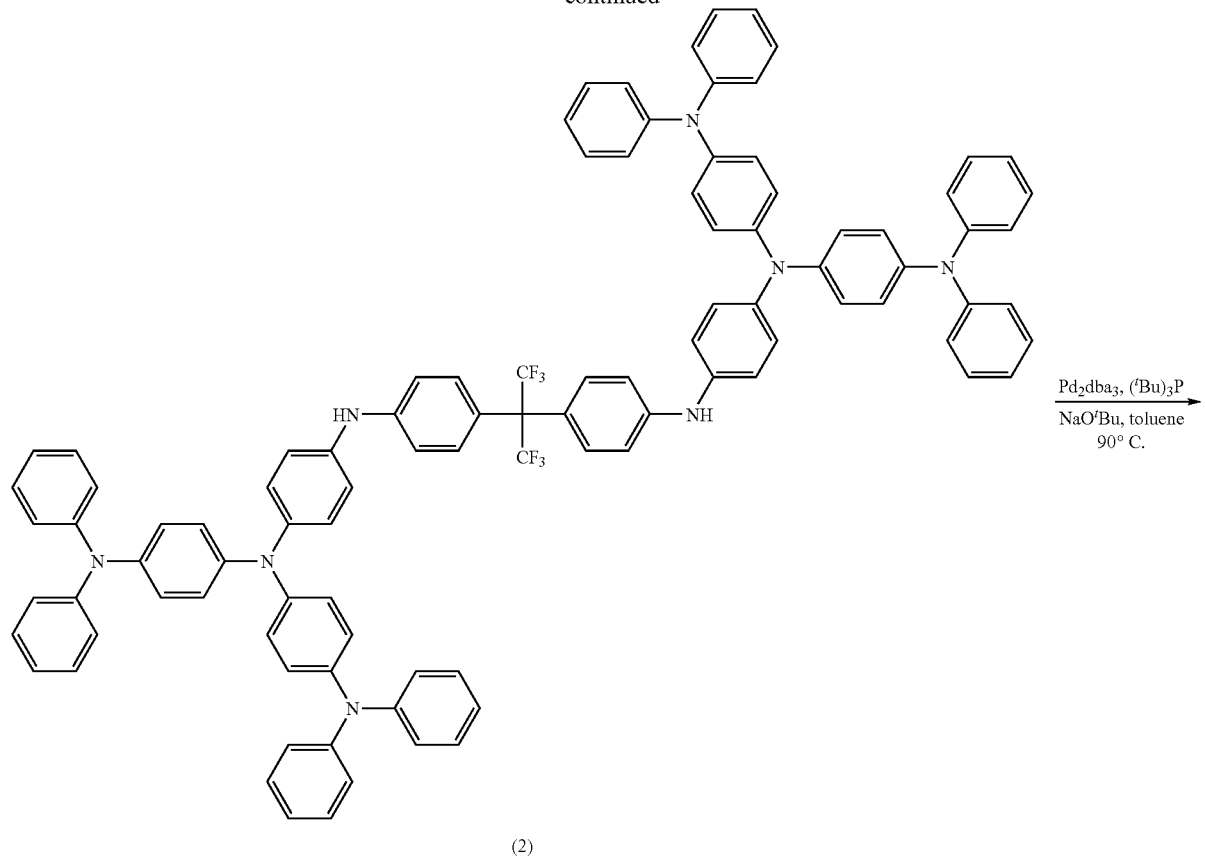
(2)
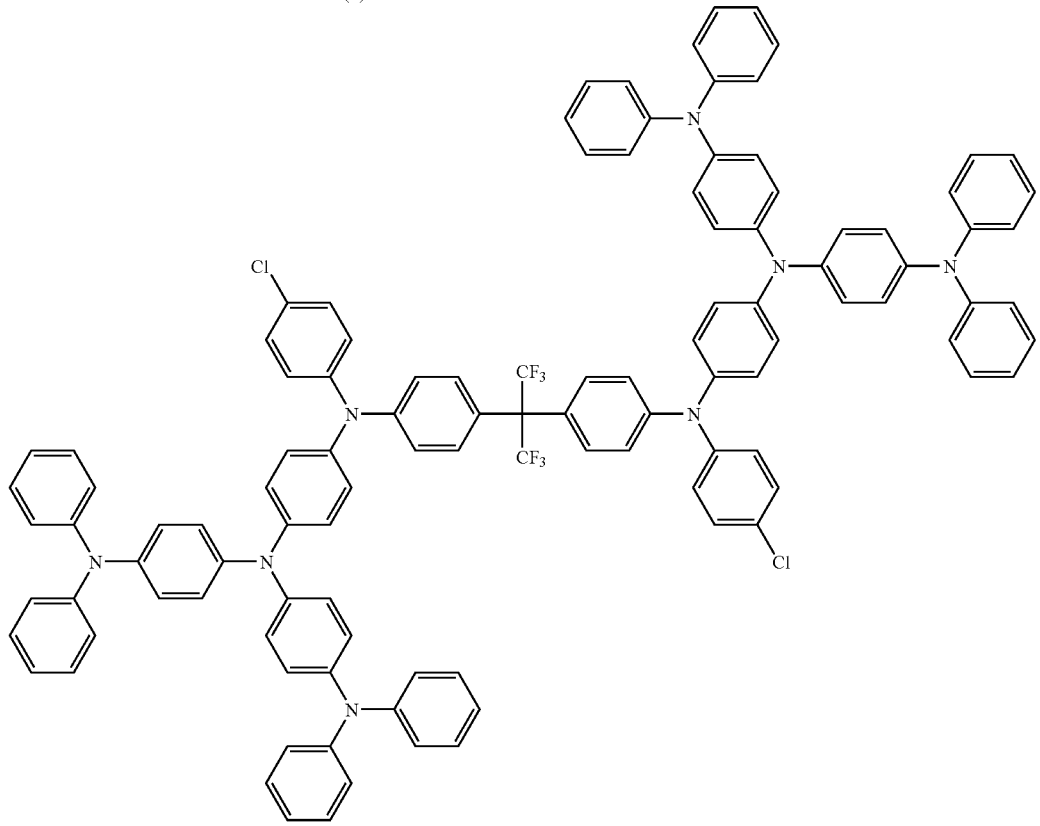
Compound 2

The reaction is carried out in a N₂ purged glovebox. Precursor (2) from Example 1 (2.85 g, 1.91 mmol), 1-chloro-4-iodobenzene (1.37 g, 5.75 mmol) and toluene (20 ml) are combined in a 100 ml round bottom flask equipped with a magnetic stirrer. Tris(dibenzylideneacetone)dipalladium(0) (88 mg, 0.096 mmol), tri-t-butylphosphine (39 mg, 0.19 mmol) and sodium t-butoxide (0.44 g, 4.6 mmol) are added and the flask is capped. The reaction is stirred at room temperature for 16.5 hours, diluted with toluene (20 ml), filtered through a plug of silica gel (10 g) topped with diatomaceous earth (25 g) and then rinsed first with dichloromethane (100 ml) and then THF (100 ml). Silica gel (18 g) is added to the combined filtrate and rinse. Solvent is removed first by rotary evaporation then under high vacuum. The product is purified by flash column chromatography on silica gel with 1:2 CH₂Cl₂/hexanes, then 1:1 CH₂Cl₂/hexanes, then CH₂Cl₂, then THF, then CH₂Cl₂ to yield 1.9 g of a yellow-brown solid. Original pad of silica gel topped with diatomaceous earth is flushed with THF (250 ml) and concentrated to give 0.7 g of a yellow solid. Combined solids are suspended in acetone (60 ml), heated at reflux under N₂ for 1.5 h, then cooled to RT. The product is isolated as a powder after filtration and acetone rinse. The product is dried under high vacuum to give 1.58 g (49%) of a light yellow solid. The 1H NMR spectrum (500 MHz, THF-d₈, TMS standard) is consistent with the formation of Monomer (4). 500 MHz $^1$H NMR of Monomer (4):

Part 2. Synthesis of Polymer 2

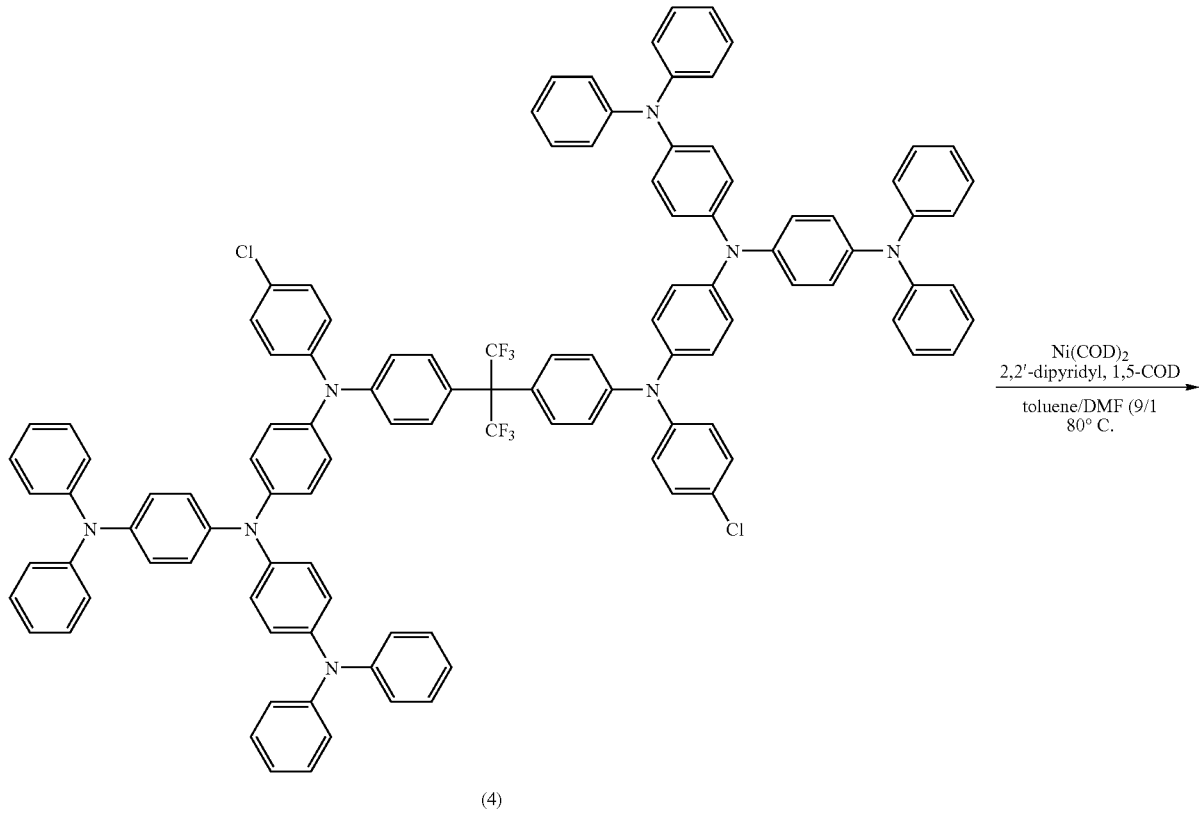

(4)

-continued

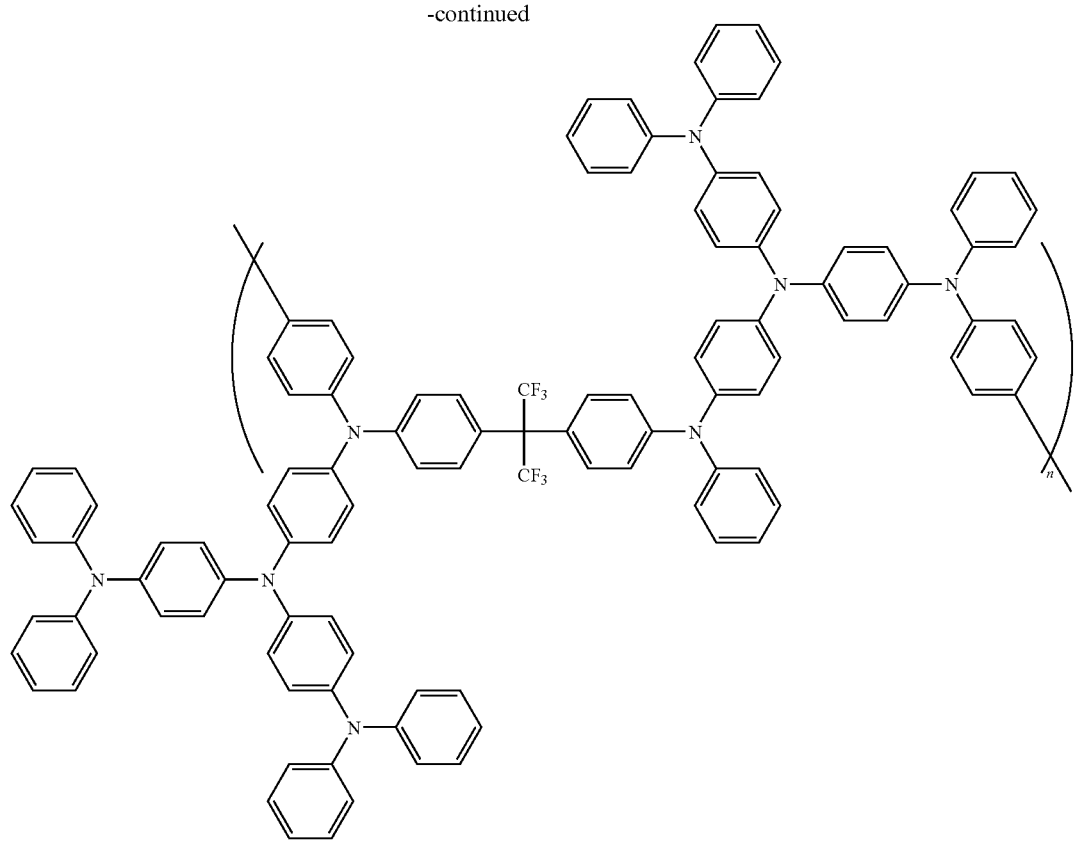

Polymer 2

Polymerization is carried out in a $N_2$ purged glovebox. Bis(1,5-cyclooctadiene)nickel(0) (0.445 g, 1.62 mmol) is added to a 25 ml Schlenk tube. 2,2'-Dipyridyl (0.253 g, 1.62 mmol) and 1,5-cyclooctadiene (0.175 g, 1.62 mmol) are dissolved in DMF (1 ml). This solution is added to the nickel catalyst. The catalyst solution is stirred and heated in an aluminum block for 15 minutes at 60° C. Monomer 4 (1.35 g, 0.789 mmol) and toluene (9 ml) are added. The tube is sealed and the temperature of the heating block is raised to 80° C. The polymerization is heated for 44 hours then cooled to room temperature. The reaction tube is removed form the dry box, conc. HCl (aq) (1 ml) is added and the contents are stirred for 1 hour. The mixture is poured into 100 ml of a 1:1 MeOH:acetone solution containing 2 ml conc. HCl (aq). The polymer is stirred and isolated by filtration, rinsing with MeOH (25 ml). The polymer is suspended in toluene (26 ml) and stirred 1 hour. The polymer solution is diluted with toluene (10 ml) and filtered through a pad of silica gel (5 g), rinsing with toluene (65 ml). The filtrate is concentrated and the polymer is purified by two precipitations into 1:1 MeOH: acetone solution containing 4 ml conc. HCl (aq), one precipitation from toluene into MeOH, one precipitation from toluene into acetone, one precipitation from THF into acetone, and one precipitation from toluene into ethyl acetate. The product is isolated by filtration and dried under high vacuum to give 910 mg (70.0%) light yellow fibrous polymer. The molecular weight determined by gel permeation chromatography (GPC, polystyrene standards) was $M_w$=119,900 and $M_n$=43,300. $^1$H NMR (500 MHz, $CDCl_3$, TMS) is consistent with the structure of Polymer 2.

Polymer 1 is made in an analogous manner.

Example 3

This example illustrates device fabrication and characterization data

OLED devices were fabricated by a combination of solution processing and thermal evaporation techniques. Patterned indium tin oxide (ITO) coated glass substrates from Thin Film Devices, Inc were used. These ITO substrates are based on Corning 1737 glass coated with 1400 Å of ITO having a sheet resistance of 30 ohms/square and 80% light transmission. The patterned ITO substrates were cleaned ultrasonically in aqueous detergent solution and rinsed with distilled water. The patterned ITO was subsequently cleaned ultrasonically in acetone, rinsed with isopropanol, and dried in a stream of nitrogen.

Immediately before device fabrication the cleaned, patterned ITO substrates were treated with $O_2$ plasma for 5 minutes. Immediately after cooling, an aqueous dispersion of Buffer 1 was spin-coated over the ITO surface and heated to remove solvent. After cooling, the substrates were then spin-coated with a solution of Hole Transport 1, and then heated to remove solvent. After cooling the substrates were spin-coated with the emissive layer solution, and heated to remove solvent. The substrates were masked and placed in a vacuum chamber. A ZrQ layer was deposited by thermal evaporation, followed by a layer of LiF. Masks were then changed in vacuo and a layer of Al was deposited by thermal evaporation. The chamber was vented, and the devices were encapsulated using a glass lid, dessicant, and UV curable epoxy.

In Example 3.1, the host was a mixture of Balq and Polymer 1. The emitter was Red emitter 1.

In Example 3.2, the host was a mixture of Balq and Compound 1. The emitter was Red emitter 1.

In Example 3.3, the host was a mixture of Balq and Compound 1. The emitter was Red emitter 2.

In Example 3.4, the host was a mixture of BAlq and Polymer 2. The emitter was Red emitter 1.

In Example 3.5, the host was a mixture of Balq and Compound 2. The emitter was Red emitter 1.

The OLED samples were characterized by measuring their (1) current-voltage (I-V) curves, (2) electroluminescence radiance versus voltage, and (3) electroluminescence spectra versus voltage. All three measurements were performed at the same time and controlled by a computer. The current efficiency of the device at a certain voltage is determined by dividing the electroluminescence radiance of the LED by the current density needed to run the device. The unit is a cd/A. The power efficiency is the current efficiency divided by the operating voltage. The unit is lm/W.

The materials used in device fabrication are listed below:

Buffer 1 was an aqueous dispersion of poly(3,4-dioxythiophene) and a polymeric fluorinated sulfonic acid. The material was prepared using a procedure similar to that described in Example 3 of published U.S. patent application no. 2004/0254297.

Hole Transport 1 was a crosslinkable polymeric hole transport material.

Red emitter 1:

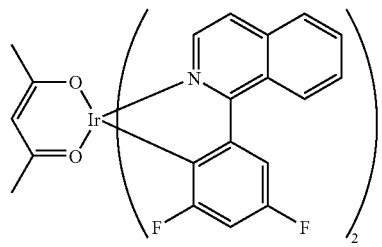

Red emitter 2:

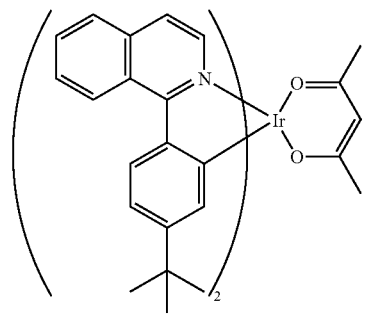

ZrQ was tetrakis(8-hydroxyquinolato)zirconium

BAlq was bis(2-methyl-8-hydroxyquinolato)(p-phenylphenolato)aluminum

TABLE 3.1

| Device characterization data | | | |
|---|---|---|---|
| | Current efficiency at 500 nits, cd/A | Power efficiency at 500 nits, lm/W | Color coordinates, (x, y) |
| Example 3.1 | 5.6 | 2.7 | (0.65, 0.34) |
| Example 3.2 | 10.3 | 5.0 | (0.65, 0.34) |
| Example 3.3 | 9.5 | 5.0 | (0.68, 0.31) |
| Example 3.4 | 7.7 | 4.0 | (0.65, 0.34) |
| Example 3.5 | 11.0 | 5.0 | (0.65, 0.34) |

Note that not all of the activities described above in the general description or the examples are required, that a portion of a specific activity may not be required, and that one or more further activities may be performed in addition to those described. Still further, the order in which activities are listed are not necessarily the order in which they are performed.

In the foregoing specification, the concepts have been described with reference to specific embodiments. However, one of ordinary skill in the art appreciates that various modifications and changes can be made without departing from the scope of the invention as set forth in the claims below. Accordingly, the specification and figures are to be regarded in an illustrative rather than a restrictive sense, and all such modifications are intended to be included within the scope of invention.

Benefits, other advantages, and solutions to problems have been described above with regard to specific embodiments. However, the benefits, advantages, solutions to problems, and any feature(s) that may cause any benefit, advantage, or solution to occur or become more pronounced are not to be construed as a critical, required, or essential feature of any or all the claims.

It is to be appreciated that certain features are, for clarity, described herein in the context of separate embodiments, may also be provided in combination in a single embodiment. Conversely, various features that are, for brevity, described in the context of a single embodiment, may also be provided separately or in any subcombination. Further, reference to values stated in ranges include each and every value within that range.

In some embodiments, the invention herein can be construed as excluding any element or process step that does not materially affect the basic and novel characteristics of the composition or process. Additionally, in some embodiments, the invention can be construed as excluding any element or process step not specified herein.

The use of numerical values in the various ranges specified herein is stated as approximations as though the minimum and maximum values within the stated ranges were both being preceded by the word "about." In this manner slight variations above and below the stated ranges can be used to achieve substantially the same results as values within the ranges. Also, the disclosure of these ranges is intended as a continuous range including every value between the minimum and maximum average values including fractional values that can result when some of components of one value are mixed with those of different value. Moreover, when broader and narrower ranges are disclosed, it is within the contemplation of this invention to match a minimum value from one range with a maximum value from another range and vice versa.

What is claimed is:

1. A compound having Formula I:

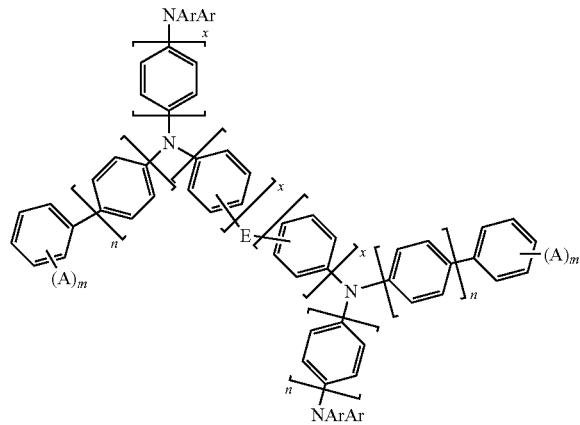

Formula I wherein:

Ar=aryl, heteroaryl, or Ar'—NAr'$_2$

Ar'=aryl, heteroaryl

A=H, D, Ar, alkyl, heteroalkyl, fluoroalkyl, or Q

E=O, S, (SiR'R")$_n$, (CR'R")$_n$, or combinations thereof, and can be different at each occurrence, wherein R' and R" are each independently selected from H, D, amide, F, alkyl, aryl, alkoxy, aryloxy, heteroalkyl, heteroaryl, fluoroalkyl, fluoroaryl, fluoroalkoxy, and fluoroaryloxy Q=a leaving group selected from halide, triflate, boronic acid, boronic acid ester, or borane m=independently, 0 to 5
n=independently, 0 to 1
x=independently, 1 to 20.

2. A polymer having at least one monomeric unit derived from the compound of claim 1, wherein at least two A=Q.

3. The compound of claim 1, wherein the compound is:

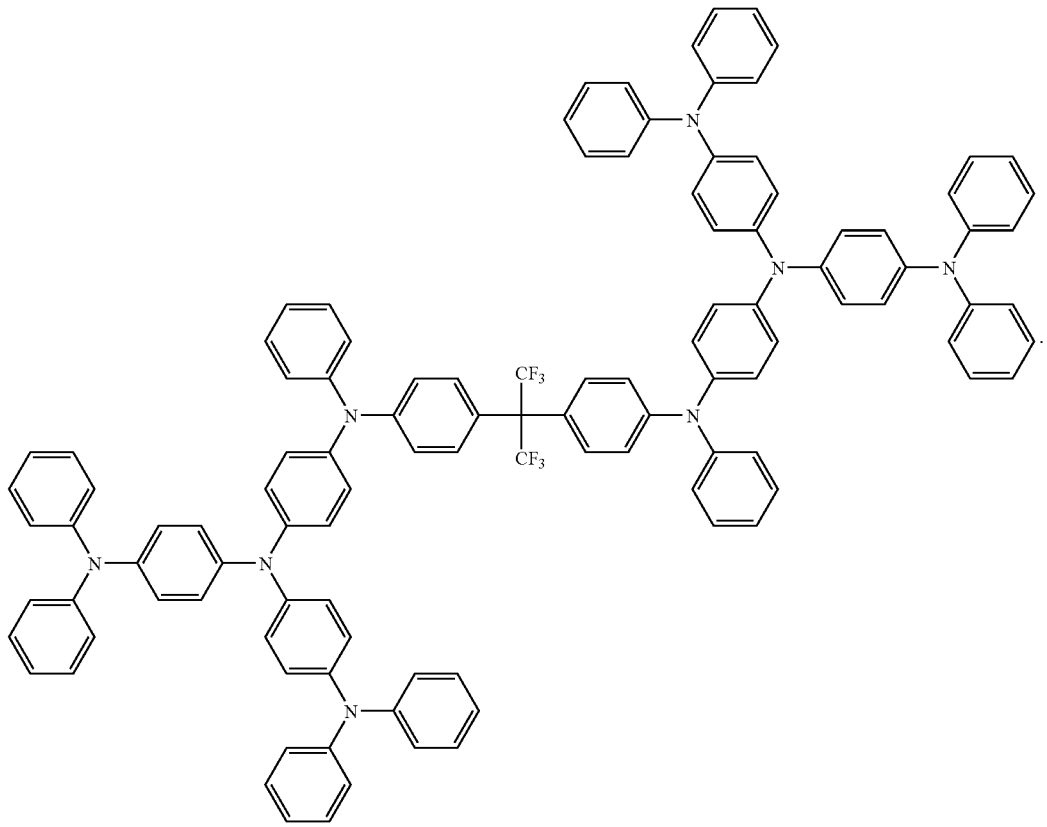

C$_{111}$H$_{82}$F$_6$N$_8$
Mol. Wt.: 1641.88

4. The polymer of claim 2 selected from the group consisting of Polymer 1 and Polymer 2:
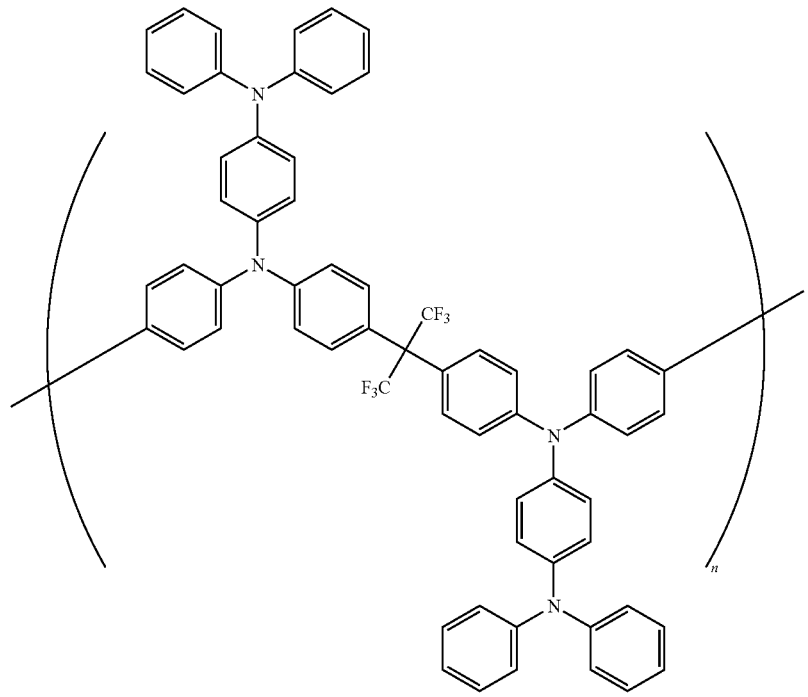
Polymer 1
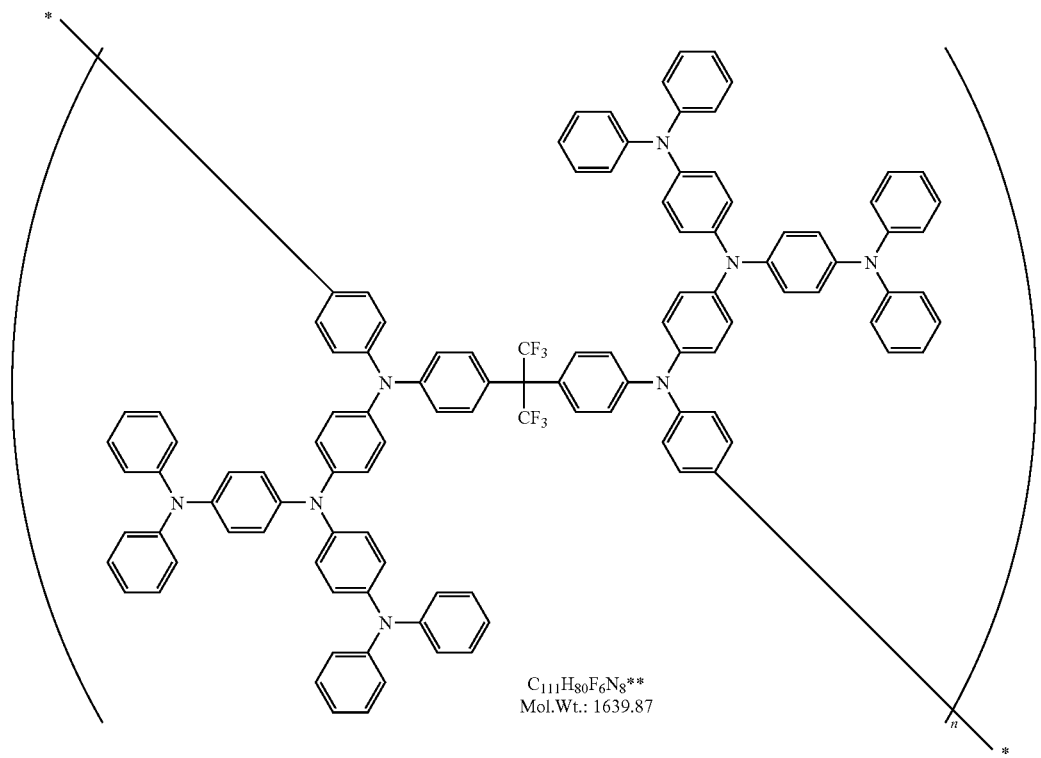
Polymer 2
$C_{111}H_{80}F_6N_8$**
Mol.Wt.: 1639.87

5. A device comprising at least one layer comprising at least one compound of claim 1.

6. A device of claim 5 wherein the at least one layer is an organic layer.

7. A device of claim 5 wherein the at least one layer is a photoactive layer.

8. A device of claim 5 wherein the at least one layer is a hole transport layer.

9. A device comprising at least one layer comprising at least one compound of claim 3.

10. A device comprising at least one layer comprising at least one polymer of claim 2.

11. A device of claim 10 wherein the at least one layer is an organic layer.

12. A device of claim 10 wherein the at least one layer is a photoactive layer.

13. A device of claim 10 wherein the at least one layer is a hole transport layer.

14. A device of claim 10 wherein the at least one polymer is selected from Polymer 1 and Polymer 2.

15. The compound of claim 1, wherein Q is Cl or Br.

* * * * *